(12) United States Patent
Berasi et al.

(10) Patent No.: US 7,763,441 B2
(45) Date of Patent: Jul. 27, 2010

(54) MODULATORS OF GLUCONEOGENESIS

(75) Inventors: Stephen Berasi, Arlington, MA (US);
Christine Huard, Somerville, MA (US);
Dongmei Li, Wayland, MA (US);
Heather Shih, Andover, MA (US); Ying Sun, Maynard, MA (US); Janet Paulsen, Londonderry, NH (US);
Eugene L. Brown, Highlands, MA (US);
Ruth Gimeno, Wellesley, MA (US);
Robert Martinez, Carlisle, MA (US)

(73) Assignee: Wyeth, Madison, NJ (US)

( * ) Notice: Subject to any disclaimer, the term of this patent is extended or adjusted under 35 U.S.C. 154(b) by 183 days.

(21) Appl. No.: 11/717,426

(22) Filed: Mar. 13, 2007

(65) Prior Publication Data
US 2007/0270331 A1 Nov. 22, 2007

Related U.S. Application Data

(60) Provisional application No. 60/781,926, filed on Mar. 13, 2006.

(51) Int. Cl.
*C12Q 1/42* (2006.01)
*C12N 9/16* (2006.01)
*G01N 33/53* (2006.01)
*A61K 38/17* (2006.01)

(52) U.S. Cl. .................... 435/21; 435/196; 435/7.2; 514/12

(58) Field of Classification Search .................... 435/21, 435/196, 7.2; 514/12
See application file for complete search history.

(56) References Cited

FOREIGN PATENT DOCUMENTS

| | | |
|---|---|---|
| EP | 1467207 | 10/2004 |
| WO | WO 01/40460 | 6/2001 |
| WO | WO 01/40798 | 6/2001 |
| WO | WO 02/24144 | 3/2002 |
| WO | WO 02/062297 | 12/2002 |
| WO | WO 2005/045032 | 5/2005 |
| WO | WO 2006/017171 | 2/2006 |

OTHER PUBLICATIONS

International Search Report on PCT/US2007/006313, mailed on Sep. 7, 2007.
Written Opinion by the ISA on PCT/US2007/006313, mailed on Sep. 7, 2007.
Lochhead P A et al, "5-Aminoimidazole-4-Carboxamide Riboside Mimics the Effects of Insulin on the Expression of the 2 Key Gluconeogenic Genes PEPCK and Glucose-6-Phosphatase", Diabetes, Jun. 2000, vol. 49, No. 6, pp. 896-903.
Ronne H, "Glucose repression in fungi", Trends in Genetics: TIG, Jan. 1995, vol. 11, No. 1, pp. 12-17.
Hardie D Grahame, "The AMP-activated protein kinase pathway—new players upstream and downstream", Journal of Cell Science, Nov. 1, 2004, vol. 117, No. Pt 23, pp. 5479-5487.

(Continued)

*Primary Examiner*—Karen Cochrane Carlson
*Assistant Examiner*—Rosanne Kosson
(74) *Attorney, Agent, or Firm*—Choate, Hall & Stewart LLP; Fangli Chen, JD; Suzanne P. Nguyen

(57) ABSTRACT

The present invention provides methods of affecting gluconeogenesis by altering the levels or activity of DUSP4 and/or EGR1. Pharmaceutical compositions comprising or encoding modulators of gluconeogenesis are also disclosed.

8 Claims, 16 Drawing Sheets

Depletion of EGR1 or DUSP4 attenuates the inhibition of glucose production by AICAR in Fao hepatoma cells

OTHER PUBLICATIONS

Berasi Stephen P et al, Inhibition of Gluconeogenesis through Transcriptional Activation of EGR1 and DUSP4 by AMP-activated Kinase, The Journal of Biological Chemistry, Sep. 15, 2006, vol. 281, No. 37, pp. 27167-27177.
Andreelli et al., Endocrinology, 2006, vol. 147, No. 5, pp. 2432-2441.
Awasthi et al., J. Virol., 2004, vol. 78, No. 12, pp. 6431-6438.
Bauer et al., Arch. Biochem. Biophys., 2005, vol. 438, No. 1, pp. 36-52.
Cao et al., J. Biol. Chem., 2005, vol. 280, No. 52, pp. 42731-42737.
Chen et al., J. Biol. Chem., 2001, vol. 276, No. 31, pp. 29440-29449.
Chu et al., J. Biol. Chem., 1996, vol. 271, No. 11, pp. 6497-6501.
Clarke et al., Embo J., 1990, vol. 9, No. 8, pp. 2439-2446.
Ding et al., J. Biol. Chem., 1995, vol. 270, No. 8, pp. 3667-3676.
Faour et al., J. Biol. Chem., 2005, vol. 280, No. 10, pp. 9536-9546.
Foretz et al., Diabetes, 2005, vol. 54, pp. 1331-1339.
Foretz et al., J. Biol. Chem., 1998, vol. 273, No. 24, pp. 14767-14771.
Graf et al., J. Biol. Chem., 1999, vol. 274, No. 17, pp. 12043-12048.
Hong et al., J. Biol. Chem., 2003, vol. 278, No. 30, pp. 27495-27501.
Inoki et al., Cell, 2003, vol. 115, pp. 577-590.
Jakobsen et al., J. Biol. Chem. 2001, vol. 276, No. 50, pp. 46912-46916.
Jorgensen et al., Diabetes, 2004, vol. 53, pp. 3074-3081.
Kawaguchi et al., Proc. Natl. Acad. Sci U.S.A., 2001, vol. 98, No. 24, pp. 13710-13715.
Kinane et al., J. Biol. Chem., 1994, vol. 269, No. 44, pp. 27503-27509.
Lee et al., J. Biol. Chem., 1995, vol. 270, No. 27, pp. 15979-15983.
Leff, Biochem. Soc. Trans., 2003, vol. 31, pp. 224-227.
Levkovitz et al., J. Neurosci., 2002, vol. 22, No. 10, pp. 3845-3854.
Myers et al., Comput. Appl. Biosci., 1988, vol. 4, No. 1, pp. 11-17.
Munday et al., Eur. J. Biochem., 1988, vol. 175, pp. 331-338.
Nakatani et al., J. Biol. Chem., 2004, vol. 279, No. 44, pp. 45803-45809.
Needleman et al., J. Mol. Biol., 1970, vol. 48, pp. 443-453.
Stefano et al., J. Neurochem., 2006, vol. 97, pp. 92-104.
Stein et al, J. Clin. Endocrinol. Metab., 2004, vol. 89, No. 6, pp. 2522-2525.
Sutherland et al., Philos. Trans. R. Soc. Lond. B. Biol. Sci., 1996, vol. 351, pp. 191-199.
Vincent et al., Diabetologia, 1996, vol. 39, pp. 1148-1155.
Winder et al., J. Appl. Physiol., 1997, vol. 82, pp. 219-225.
Wu et al., Curr. Drug Targets Immune Endocr. Metabol. Disord., 2005, vol. 5, pp. 51-59.
Xu et al., J. Biol. Chem., 2003, vol. 278, No. 32, pp. 30187-30192.
Yang et al., J. Biol. Chem., 2001, vol. 276, No. 42, pp. 38341-38344.
Zhang et al., J. Biol. Chem., 2001, vol. 276, No. 49, pp. 45604-45613.
Zhang et al., J. Lipid Res., 2002, vol. 43, pp. 1477-1485.

Eisen clustered display of expression data of AICAR stimulated AML12 hepatocytes over time EGR1 is induced by AICAR in H4IIE hepatocytes DUSP4 is induced by AICAR in H4IIE hepatocytes EGR1 binds to the rat DUSP4 promoter following treatment with AICAR EGR1 and DUSP4 expression levels affect PEPCK promoter activity EGR1 and DUSP4 expression levels affect PEPCK promoter activity EGR1 and DUSP4 expression levels affect PEPCK promoter activity Depletion of EGR1 or DUSP4 attenuates the inhibition of glucose production by AICAR in Fao hepatoma cells

DUSP4 represses PEPCK through regulation of p38

DUSP4 represses PEPCK through regulation of p38

Model of repression of glucose production by AICAR

FIGURE 9

```
   1 gctgagcgcc ggaggagcgt aggcagggca gcgctggcgc cagtggcgac aggagccgcg
  61 cgaccggcaa aaatacacgg gaggccgtcg ccgaaaagag tccgcggtcc tctctcgtaa
 121 acacactctc ctccaccggc gcctccccct ccgctctgcg cgccgcccgg ctgggcgccc
 181 gaggccgctc cgactgctat gtgaccgcga ggctgcggga ggaaggggac agggaagaag
 241 aggctctccc gcgggagccc ttgaggacca agtttgcggc cacttctgca ggcgtcccct
 301 cttagctctc gcccgcccct ttctgcagcc taggcggccc gggttctctt ctcttcctcg
 361 cgcgcccagc cgcctcggtt cccggcgacc atggtgacga tggaggagct gcgggagatg
 421 gactgcagtg tgctcaaaag gctgatgaac cgggacgaga atggcggcgg cgcgggcggc
 481 agcggcagcc acggcaccct ggggctgccg agcggcggca agtgcctgct gctggactgc
 541 agaccgttcc tggcgcacag cgcgggctac atcctaggtt cggtcaacgt gcgctgtaac
 601 accatcgtgc ggcggcgggc taagggctcc gtgagcctgg agcagatcct gcccgccgag
 661 gaggaggtac gcgccgctt gcgctccggc ctctactcgg cggtcatcgt ctacgacgag
 721 cgcagcccgc gcgccgagag cctccgcgag gacagcaccg tgtcgctggt ggtgcaggcg
 781 ctgcgccgca cgccgagcg caccgacatc tgcctgctca aggcggcta tgagaggttt
 841 tcctccgagt acccagaatt ctgttctaaa accaaggccc tggcagccat cccacccccg
 901 gttccccca gtgccacaga gcccttggac ctgggctgca gctcctgtgg gaccccacta
 961 cacgaccagg ggggtcctgt ggagatcctt cccttcctct acctcggcag tgcctaccat
1021 gctgcccgga gagacatgct ggacgccctg gcatcacgg ctctgttgaa tgtctcctcg
1081 gactgcccaa accactttga aggacactat cagtacaagt gcatcccagt ggaagataac
1141 cacaaggccg acatcagctc ctggttcatg gaagccatag agtacatcga tgccgtgaag
1201 gactgccgtg ggcgcgtgct ggtgcactgc caggcgggca tctcgcggtc ggccaccatc
1261 tgcctggcct acctgatgat gaagaaacgg gtgaggctgg aggaggcctt cgagttcgtt
1321 aagcagcgcc gcagcatcat ctcgcccaac ttcagcttca tggggcagct gctgcagttc
1381 gagtcccagg tgctggccac gtcctgtgct gcggaggctg ctagcccctc gggaccctg
1441 cgggagcggg gcaagacccc cgccacccc acctcgcagt tcgtcttcag cttttccggtc
1501 tccgtgggcg tgcactcggc ccccagcagc ctgccctacc tgcacagccc catcaccacc
1561 tctcccagct gttagagccg ccctggggc cccagaacca gagctggctc ccagcaaggg
1621 taggacgggc cgcatgcggg cagaaagttg ggactgagca gctgggagca ggcgaccgag
1681 ctccttcccc atcatttctc cttggccaac gacgaggcca gccagaatgg caataaggac
1741 tccgaataca taataaaagc aaacagaaca ctccaactta gagcaataac ggctgccgca
1801 gcagccaggg aagaccttgg tttggtttat gtgtcagttt cacttttccg atagaaattt
1861 cttacctcat ttttttaagc agtaaggctt gaagtgatga acccacaga tcctagcaaa
1921 tgtgcccaac cagctttact aaaggggag gaagggaggg caaagggatg agaagacaag
1981 tttcccagaa gtgcctggtt ctgtgtactt gtcccttttgt tgtcgttgtt gtagttaaag
2041 gaatttcatt ttttaaaaga aatcttcgaa ggtgtggttt tcatttctca gtcaccaaca
2101 gatgaataat tatgcttaat aataaagtat ttattaagac tttcttcaga gtatgaaagt
2161 acaaaaagtc tagttacagt ggatttagaa tatatttatg ttgatgtcaa acagctgagc
2221 accgtagcat gcagatgtca aggcagttag gaagtaaatg gtgtcttgta gatatgtgca
2281 aggtagcatg atgagcaact tgagtttgtt gccactgaga agcaggcggg ttgggtggga
2341 ggaggaagaa agggaagaat taggtttgaa ttgcttttta aaaaaaaag aaaagaaaaa
2401 gacagcatct cactatgttg ccaaggctca tcttgagaag caggcgggtt gggtggggagg
2461 aggaagaaag ggaagaatta ggtttgaatt gctttttt (SEQ ID NO:12)
```

Figure 10

```
dusp4.rat    ------------------------------------------------------------
dusp4.human  GCGGCTTTGACCACTGATCTCCCACCCGGAGTGCCCGACGCCCAGGTCCTGCCACCGGG    60 dusp4.rat    ------------------------------------------------------------
dusp4.human  CAGCCTCGGTCAGTCCACAGTTGTGGCTCCTTCCAGGGCCTGGACTAGGGTGAGCACAAG   120 dusp4.rat    ------------------------------------------------------------
dusp4.human  CCTTGAGCGCAACATTTAAGAAGGGCGCCGAAAAGTCAGTAATCAAAAGAAATATCTTGA   180 dusp4.rat    -----------------------AATAGCTCATTCTTTAACTGAAAA--AAC           27
dusp4.human  TGCAATGCCTCTCTTTAAAGAAAAAAAAAATGCAAAAAATCCATGATGAATAAAATACTAAA  240
                                    *       *    * dusp4.rat    CCATAAAACAAAATAAGAAAC---GCAGTGCCAT----------TTTGGAACCCAAGGTAA   74
dusp4.human  TTTTAAAAAGAGAAAAGGATCCGTCAGTGCCATCGTAAGCCATTTGGAGCCCGGAGCAA    300
             *  **    ***   *    ******               * * dusp4.rat    CAAGGAAAATTCTC---CACAGATGATTGCCCCCTGCAACGCCCA--CTGGACCCAGAAA    129
dusp4.human  AAGGAAATATCACCTTGCCCAAGCGTGCCCAGTCGGGGACGAGGCCAGTCGAGTAGGGCCCGGGGG   360
              ****   *    ** *  *  **   *    * **  * *** * dusp4.rat    --AGGGTGTTGGGGACTTCAGAGTGCAGAGAGTCTGTAGGAAGCCTTGAAAATGGGAGTT   187
dusp4.human  TCGAGGCATTCGGGGCCCAGTGGGGCCCCAGTGGGGACGAGGCCAGTGGAAGGTCTCGGAAGGCT   420
                 * **  * *    **  *     *   **** * * dusp4.rat    ------------GGAGGTGATCTCTGGAGAGCCGCTCTGCA--------GAAAACAAAG   226
dusp4.human  CCGCCGAGCTCCGGTCGGGGAGTCGGGGATGCAGGGATGGCCCCCCGGGACCGGAGGTGAGAGCTCGG   480
                          **  *  *   *  *                 **  *  ***  * dusp4.rat    CAAAG-------GTAACTGAG---TGGAGAGAGGGTTTAACCGGG-GGAAAGGACC      271
dusp4.human  GAAAGCCGCTCCGCCCGGAACAAAGGCATGGGGAGAGGGTGAGCTTGGGCGGGAGAGACC   540
             ****          *    *            *  ** *  **** dusp4.rat    CTGAGGCTTTGGCTGCCCTGCCCTCCGCTGCCTCAGTCAGGCTTCAGGCTTCTACTCGCAACCTGAAATGGAA   331
dusp4.human  CGGCGGGTACCGGTGCCCGGTGCCCTGCCTGCCTGGTCGGGCTTCCACGCGGCGGCCGCCCCGGAATGGAA    600
             *  *     *  ******     *   * * *       *****       ***    ** ********
``` dusp4.rat
dusp4.human

Figure 10 (continued)

```
dusp4.rat    TATTCGACCTGGCCGCGCTACCAAA---------CCCCGTAATTCCCTTGTTCGGTGAT  379
dusp4.human  TACGCTACTCTGCAGCCTCGAAACTGCGAGCGAGTCCTGTAACTCCCTTGCTCTGTGAT  660
             **  *  ***  *            *****  *  ****  ***** dusp4.rat    TAATTCTTGCTAACAGAGACTTGGCAAGATCTCGGCCGAATAATTTTTGGCTTCTGTAAGG  439
dusp4.human  TAATTCTCACTAACAGAGACTTGGCAAGATGTCGGGCGAATGATTTTTGGCTTCTGCACGG  720
             *****  ****************  * ********** dusp4.rat    TCCCCACCACATGCGCCGCATAACCTCCTTTCTGCCAAAATCAAGCCCTTGGGAAATTAA  499
dusp4.human  TCCCCACCGCGTGCGTGCCGTGCACAAACCCCCA-----GCCAAAGCC-GCCTCTGGGAAATTAA  775
             ******** * *** * *    ** *       *  *** *    ************* dusp4.rat    ATGTCCCCGGGAAGGTAAAAGCGGGGTGCAGATGCTACGTGCAGATGTGACCTGAAAAGAGGATGT-  558
dusp4.human  ATGCAAAAGAGAAA-TGGGGATGGGGAG--GGCTGCTACGTGACCAGAAAAAGGGATGCC  833
             ***     *  *   * **   *  *********  ** dusp4.rat    -AGAAACTCGAATCGTCTCTGAGCTTATTAAATTGCCTTTAAAAGGTCACTCTTCGCA  617
dusp4.human  CAGAAACATGAATCGGACCCAGAGCTGCTGAAGT--CCTTTCAAAAGGTCATTCTTTGCG  891
             ****  ****    **        ***  ** dusp4.rat    TGGACACTTTTCAACACATCTTCCTTCGCACCAAATGTAGACCTTAACAATTATTCCTTAG  677
dusp4.human  GGTACATTTTCCAGGGTCCAGCTCCGCAACAAATGTGGACCCT----GTCATTCCTGAA  947
             *  * **** *  ** *  * **** ***      *  ** dusp4.rat    AGGACATTGCGTG--TGAGCAAGAGGGAGGCGAGGACTTCCACCAAAGCGGAAAACCTCC  735
dusp4.human  AGGATAATTCACACATGCAAGTAGCAAGATAG--GGTGAAGACGTTTCCCAAACCCGAAACCT--  1004
             ****     *  *  *  *  *      *        ****** dusp4.rat    GGGTATATCCCTCCCTCCCCCCCTTCCATGGTTAAATAATCAGGTTTTAGGAAGCTTGGG  795
dusp4.human  ---------TGTTTTTCCCCCGACCAGGGTTAAATAAACATCTTTTAGGAAGCGTGA  1053
                      * *   *  ***       ****   **********  * * dusp4.rat    CCGGAGTGCTTCCCATTCTCCGCACGGCACACCATTCGGCCAATTAACGCCCCCCTCT  855
dusp4.human  CAGGAGCGCAGCCGCAGCCTCTGCTCTCCCTGCACGGAACACCATTCCGGCAATTAATGCCTCCCTTT  1113
             * **                  ******  * *** * * ** dusp4.rat    GGGTTGTAAAGTAACAAACCCCTACACCTCTCTTTTGTATTGGCTTTGGCGCGGAGGAC  915
dusp4.human  GGGTAGTAAAGCAACAAAACCCC--ACACCTCACTCCAGATCCTCGATCCGGCTTCGGGCCGGGGAGGAC  1172
             ** ***  *       ***      *    *    * * ****** dusp4.rat    TTCC-CTTTCATCTTTCAAAGTCCGGGGTTTGCCCAGGTTCCGCGGAAGCTATAAAACC  974
dusp4.human  TTTCTCTTTCATCTTCCAAG--CAGGGGGTTGCCCACGTCTTGGGAAGCTATAAAAACT  1230
             ** * **********  ***    ***** ******  *  ****************
```

Figure 10 (continued)

```
                 ** * *********** *** * **** ******** ****         *****************
dusp4.rat        GATCTAATAGCTCCGGACGGAAATCGATCACGCAAATGTATAAACTAA-GTCCGGGGAAT 1033
dusp4.human      GATTTAATGGCTTTAGATGAAAATCGATCACGCTAATGCATACGCTAACGTCTCAGGAAT 1290
                 * *     ******** *  *     ** dusp4.rat        CGCATTAAAAACAAAAACAAGACACACAACCGGCCGACCCGAAGAGCAAGCTTTAGTCCGGC 1093
dusp4.human      CGCAT-------ATTCAGAAAGGACTGGCCGGGCCGAAAGCGCACGGG-AGTCTGGG 1340
                 *****         *  * *  *  * **  *** *     *  * dusp4.rat        GAGAAGAGGTCCCAAGCCCTGCGGGGTGG-CAGCCATACAGTG--TCAGGTTCCACCCAG 1150
dusp4.human      GCTAGGAGGTGTCAGGCCCCGCTGGGTGGGCAGCAGCCTCCGGTCCCCTCTCCACTTGG 1400
                 *  * *   *   *** ***   * *      *  ****** * dusp4.rat        CGAGACCTCGGAGAGACTTGGGGGGCGGG-----GGGGGAGCGCAGGGGTG--AAGACCTCC 1203
dusp4.human      GTAACCGGGAAAAAACCTACGGGGCTGTCACGCGGGAGAAGCGCGAAGGTGCCAAGGGATGA 1460
                 *  ****   *        *  * *      *     *   * * dusp4.rat        ACGCTGA------GAGCCCAGGCCTC------GGTTAGGCCCGC-GTCGCCACCCGC--- 1247
dusp4.human      AAGCTCAAAACCCGAGCCCTGGCCTCCTCAGCCGGCTATTTCCTTTGGCGCCGCCCGCCTA 1520
                 * *** *      *****           * * ** **** dusp4.rat        ---------------TACTAACACAACGCCGAACGC----CGCGCTCCG         1277
dusp4.human      GCGGCGGGGTGCAGGCGGCGGCACAGTGCCGTGTCGGGCGTGAGGCGGCGGCCAGGCTG 1580
                                * * **  *  *  * dusp4.rat        GGGCTGAGGAAGGACAGGGAGCCGCACGGCG-GCTCCATTCACAAAGTCCGGGAGCTTCC 1336
dusp4.human      GGCCCGCGGGCTAGACGGGCGGAAAGGCGCCCGCCGCCTCCATTCACAAAGTCCGGGCGCTGCC 1640
                 **  *  *  * ***  *     *     * ************    ** dusp4.rat        GGCT--TGCCGGCGGGTCGGAGGCTGCCTGCCTCCTTTTCCTCTAGGTCTCGGTTTTATGAAT 1394
dusp4.human      CGCCGCTGCCGCGGGTCGGAGGCGGGAGGCGCCGCCGCTCCTCGGCCCTCGGTTTTATGAAT 1700
                 * *   ***** ****    ***  *    *  ***************** dusp4.rat        GGGCCTGGCAGACAGCACCGAGCGCCCCTGTTTACTCCTCTCTTTGTGACGTCGAGTTCCC 1454
dusp4.human      GGGCCTGATGGGCGAGCACCCGGCGCCCTTACTCCGCTCTTTTGTGACGTCGAGTTCCC 1760
                 *******   *  * *  **  *   **** ************** dusp4.rat        GTGACTGGGTGCGAGGGGGCCGGGGCCCGGCCTCCATTCAAGAGTCGGGGTGGGGCGCGGGG 1514
dusp4.human      GTGACCGGGGAGCCAGCCAGCCGCC--GCGCTCCATTCAAGCTCCGGGGAGGGGTGGGAGGAGG 1818
                 ***** ***  **  ***  **      ***  *************   ***** *** ***
```

Figure 10 (continued)

```
dusp4.rat    AGCTTGCGTGGGGGGCGGGGCCTGGAGAGGTAGTAATGACTCTTCCCTCCCCCGGGAGAG  1574
dusp4.human  GGCCCCGGAGGGGGGCGGGGAGTCAGCGCGGGGGCGGGGGA-------CAGCGCGGGGG  1869
             **  *  **                  *  ****  *    *** * * dusp4.rat    CCGGCGAGCATTAATAAATCTCTAAGCAGAGGAGAAACTCTCGCTGGGCAGTGCGTGC  1634
dusp4.human  GCGGGGACGGCGCGGGCCCGAATGGAACGGGGCCTGGCGGGGGTAGTACCTAG  1929
             *     *       *   *    * *   *     ****  * dusp4.rat    AGCTCCGGC------GGAGCGTTGGGGAAAAACGGCGGTGCCTAAGGC--AGGAGCAG--C  1685
dusp4.human  CGCCCCCTCCCCCGGGAGCGGGAGCGCCGGAGAGCATTAATAAACCTCTAAGCCGAGGAGAAAACT  1989
             * *   *       ******  *    * *              *     * *  **** * dusp4.rat    CTAGCTAGCAAAACACACCAGGGGC--AACAAACCGAGAGGAGCCCTCTCTCTCGTAAAC  1743
dusp4.human  CTGGCTGGGCAGTGCCGCTGAGCGCCCGAGAGCGTAGGCAGGGCAGCGCTGCGCCAGT  2049
              *  *  **  *  *        *    **  *      ****   *    * dusp4.rat    ATACTCCCCTCCTCGGTCACTTGCTCCGGGTGCCGTGCGCCCGCCTGCTTTGGCGCCAGA  1803
dusp4.human  G------------------------------------------------------------  2050 dusp4.rat    GAAGGCTCGGACTGCTATGTAACGTCGAGGCTGCGGGAGGAGGAGGAAGGGGTGTTGGGA  1863
dusp4.human  ------------------------------------------------------------ dusp4.rat    GAAGAGCCTTGGGGCCAAGTTTGCGGGTCACTTCGGCAGGCGCCTTCTTAGCCTTCGCCT  1923
dusp4.human  ------------------------------------------------------------ dusp4.rat    GTTCCTTCTTGTAGCCTAGCTGGCTTGGGTGCCCTTGGTCTTCTCCGGCTCCCCAGCTGC  1983
dusp4.human  ------------------------------------------------------------ dusp4.rat    TGTGCTTTGCCGGCGACATGGTGACGATGGAGGAACTGCGCGGAGATGGACTGCAGCGTGC  2043
dusp4.human  ------------------------------------------------------------ dusp4.rat    TCAAAAAG  2050     (SEQ ID NO:13)
dusp4.human  --------          (SEQ ID NO:14)
```

MODULATORS OF GLUCONEOGENESIS

CROSS-REFERENCE TO RELATED APPLICATIONS

This application claims priority to and the benefit of U.S. Provisional Patent Application No. 60/781,926, filed on Mar. 13, 2006, the entire contents of which are incorporated by reference herein.

FIELD OF THE INVENTION

The present invention relates to compositions and methods for the control of blood glucose levels.

BACKGROUND OF THE INVENTION

Understanding the pathways that maintain proper glucose homeostasis is a central focus of discovery efforts for treatments of Type 2 diabetes which now affects over 20 million Americans, with levels increasing at 6% a year (Stein et al. (2004) *J. Clin. Endocrinol. Metab.* 89:2522-2525). Proper glucose homeostasis requires a balance between glucose uptake by skeletal muscle and adipose tissue, and production by the liver. Type 2 diabetic patients lose this balance due to a reduction of glucose uptake during the fed state, as well as improper fasting gluconeogenesis by the liver. During the fasted state, glucagon secretion by the pancreas and resulting cAMP mediated signaling through CREB, as well as glucocorticoid release, result in gluconeogenic gene transcription. In the fed state this transcriptional program is suppressed by insulin signaling due to repression of the nuclear hormone receptor co-activator PGC-1α, which is necessary for CREB mediated transcription. Phosphoenolpyruvate carboxykinase (PEPCK) and glucose-6-phosphatase (G6P) are two rate-limiting enzymes for gluconeogenesis that are transcriptionally regulated by glucagon and insulin, and are widely used as markers for gluconeogenesis (Sutherland et al. (1996) *Philos. Trans. R. Soc. Lond. B. Biol. Sci.* 351,:91-199).

Due to the important role of dysregulated gluconeogenesis in the pathology of Type 2 diabetes, further insight into the mechanisms of repression of these genes by insulin independent mechanisms could lead to treatments of insulin resistant individuals (Wu et al. (2005) *Curr. Drug Targets Immune Endocr. Metabol. Disord.* 5:51-59). Activation of AMPK (AMP activated kinase) is one insulin independent means of gluconeogenesis repression. AMPK has been termed a "master switch" of cellular energy status, being highly conserved from simple eukaryotes to humans. In mammalian systems it is activated in multiple organs during conditions that cause a low ATP/AMP ratio. These include exercise and starvation on the whole body level as well as many cellular stresses such as glucose deprivation, oxidative stress, ischemia, and exposure to metabolic poisons that inhibit ATP synthesis (Hardie et al. (2003) *FEBS Lett.* 546:113-120; Hardie (2004) *J. Cell Sci.* 117:5479-5487). When activated, AMPK switches on ATP generating processes and switches off those that consume ATP. In vivo and in vitro there is much evidence indicating that AMPK activation inhibits gluconeogenesis (Foretz et al. (1998) *J. Biol. Chem.* 273:14767-14771). Treatment of rat hepatoma cells or primary hepatocytes with the AMPK activator AICAR inhibits expression G6P and PEPCK (Lochhead et al. (2000) *Diabetes* 49:896-903). In vivo, activation of AMPK in the livers of fasted mice has been shown to reduce glucose production (Vincent et al. (1996) *Diabetologia* 39:1148-1155) and gluconeogenic gene expression (Foretz et al. (2005) *Diabetes* 54:1331-1339). Additionally, AMPK has been suggested to mediate the beneficial and detrimental effects of adiponectin and resistin, respectively, on hepatic glucose output. Recently this has been supported by the finding that genetic deletion of the AMPK alpha2 isoform in the mouse liver leads to glucose intolerance and hyperglycemia in the fasted state, which could be reversed by insulin. Yet, these animals were resistant to regulation of glucose production by the AMPK activators leptin and adiponectin (Andreelli et al. (2006) *Endocrinology*, en.2005-0898).

AMPK achieves its downstream effects by immediate direct phosphorylation of enzyme substrates as well as long-term effects on gene expression. For example, AMPK phosphorylates and inactivates acetyl CoA carboxylase, resulting in a suppression of the conversion of acetyl CoA to malonyl CoA. The lower levels of malonyl CoA allows entry of fatty acids into the mitochondria and their subsequent oxidation (Winder et al. (1997) *J. Appl. Physiol.* 82:219-225; Munday et al. (1988) *Eur. J. Biochem.* 175:331-338). Other direct targets that can be phosphorylated by AMPK include glycogen synthase, IRS-1, and HMG-CoA reductase (Jorgensen et al. (2004) *Diabetes* 53:3074-3081; Jakobsen et al. (2001) *J. Biol. Chem.* 276:46912-46916; Clarke et al. (1990) *EMBO J.* 9:2439-2446). AMPK's effects on transcription, and their role in mediating the physiological effects of AMPK activation are much less well understood, although it has been shown that AMPK activation decreases HNF4 expression levels leading to repression of its target genes including HNF-1alpha, GLUT2, and L-type pyruvate kinase (Hong et al. (2003) *J. Biol. Chem.* 278:27495-27501).

SUMMARY OF THE INVENTION

There remains a need for new methods and compositions for treating Type 2 diabetes. The present invention meets this and other needs.

The immediate early response transcription factor Early Growth Response 1 (EGR1) and the Dual Specificity Phosphatase 4 (DUSP4) are transcriptional targets of AMPK that are necessary for its ability to fully repress glucose production. When induced, EGR1 binds the DUSP4 promoter. In contrast, depletion of EGR1 also depletes DUSP4 levels. DUSP4 over-expression inhibits the promoter activity of gluconeogenic enzymes. Conversely, depletion of EGR1 or DUSP4 partially relieves the inhibition of glucose production by AICAR.

Accordingly, the invention permits the modulation of gluconeogenesis and of transcription of gluconeogenesis genes by altering EGR1 and/or DUSP4 activities. Gluconeogenesis can be repressed in a patient with a disorder characterized by excessive gluconeogenesis or impaired glucose tolerance, such as diabetes, by increasing a DUSP4 activity and does not require a prior increase in AMPK activity. This can involve, for example, increasing an EGR1 activity, by administering an EGR1 polypeptide, for example, to promote DUSP4 expression. As used herein, "EGR1 polypeptide" refers to any polypeptide with endogenous EGR1 activity, or any polypeptide capable of binding to the sequence CGTGACCGG-GAGC (SEQ ID NO:5) and of promoting transcription of human DUSP4. Administration can be in the form of a protein or in the form of a nucleic acid encoding or otherwise promoting expression of the protein. Administration of an EGR1 cofactor can also promote EGR1 activity. Overexpression of an EGR1 polypeptide acts synergistically with other stimuli to reduce gluconeogenesis. A reduction in gluconeogenesis can also be achieved by administering a DUSP4 polypeptide (e.g. as a purified protein or as a nucleic acid encoding the protein). As used herein, "DUSP4 polypeptide" refers to any polypeptide with DUSP4 activity, i.e. a polypeptide that, or by overexpression of a polypeptide with DUSP4 activity.

The invention also permits the promotion of gluconeogenesis in a patient who would benefit from increased glucose production, such as a patient with a glucose homeostasis disorder such as anorexia or cachexia. The promotion of gluconeogenesis can involve decreasing DUSP4 activity, which need not be preceded by a decrease in AMPK activity, and can involve administering a nucleic acid such as, for example: an RNA inhibitor (e.g. siRNA, shRNA, or microRNA) of the human EGR1 or DUSP4 gene; a DNA encoding such an RNA inhibitor, or a nucleic acid encoding a polypeptide encoding an EGR1 or DUSP4 inhibitor, such as a dominant negative form of either protein.

The invention also provides pharmaceutical compositions for modulating gluconeogenesis. The pharmaceutical compositions include a pharmaceutically acceptable carrier and one or more active ingredients, such as an EGR1 polypeptide or a nucleic acid encoding one; a DUSP4 polypeptide or a nucleic acid encoding one; an RNA inhibitor (e.g. siRNA, shRNA, or microRNA) of the human EGR1 or DUSP4 gene; a DNA encoding such an RNA inhibitor, or a nucleic acid encoding a polypeptide that inhibits EGR1 or DUSP4 proteins, such as a dominant negative form of either protein; or a combination of the above.

Other features, objects, and advantages of the present invention are apparent in the detailed description that follows. It should be understood, however, that the detailed description, while indicating preferred embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

FIG. 9 is the sequence of the human DUSP4 gene (SEQ ID NO:12). The coding sequence is from nucleotide 391 to nucleotide 1575.

FIG. 10 is an alignment of selected portions of the human (SEQ ID NO:14) and rat (SEQ ID NO:13) DUSP4 promoters. The EGR1 binding site is depicted in boldface type.

DETAILED DESCRIPTION

Figure 1:
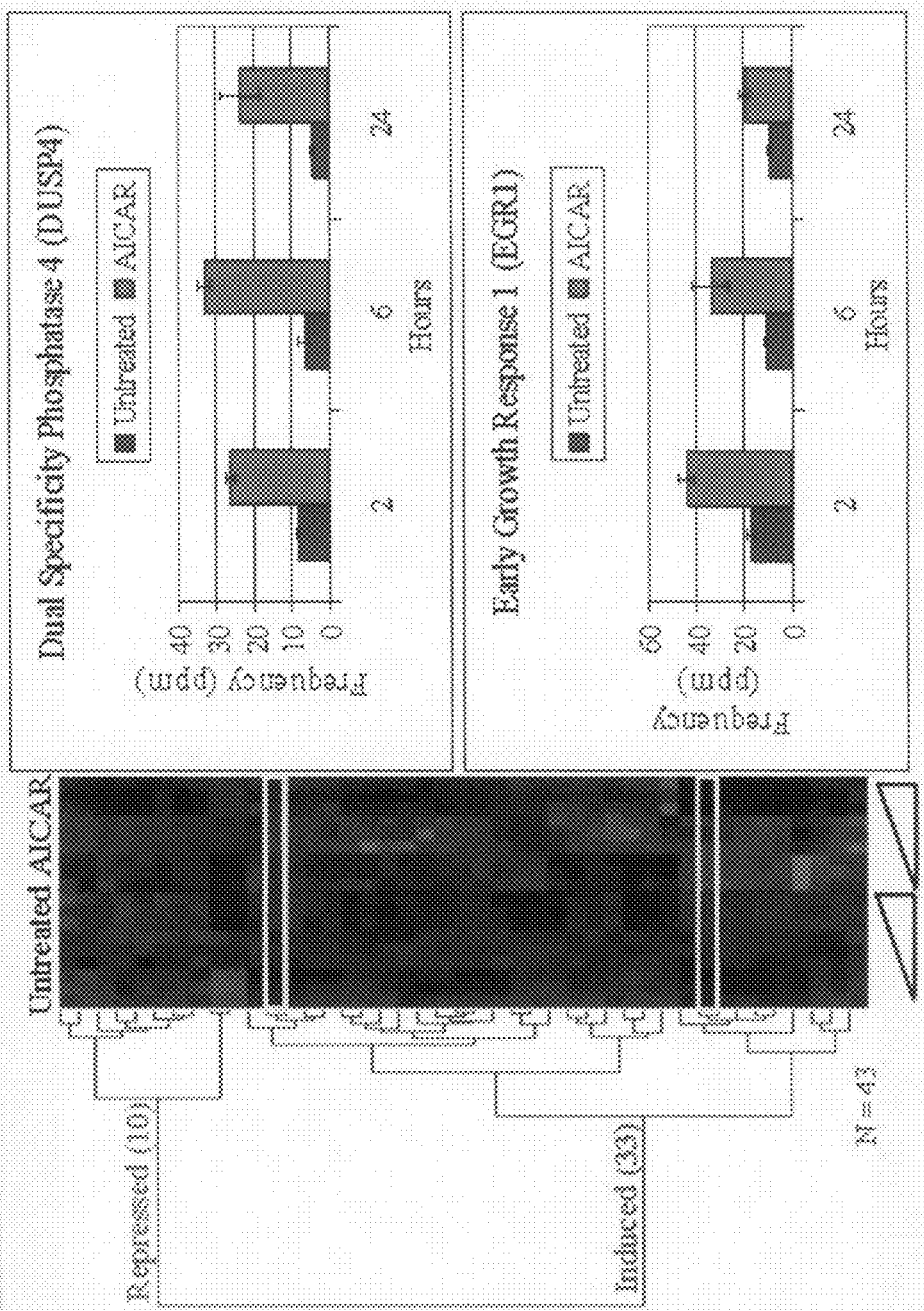
FIG. 1 schematically illustrates an Eisen clustered display of expression data of AICAR-stimulated AML12 hepatocytes over time. Genes were selected for this analysis if their expression level was statistically significantly different (p-value≦0.05) between AICAR and untreated matched time points at 2, 6 and 24 hours. Each gene is represented by a single row and each sample, in triplicate at each time point, by a column. Two distinct clusters indicate genes induced (red) and repressed (blue) by 500 µM AICAR. The mean expression±STD of DUSP4 (qualifier #1428834_at) and EGR1 (qualifier #1417065_at) are illustrated graphically as well as highlighted in yellow on the cluster.

The present invention provides new methods for treatment of type 2 diabetes. In particular, the present invention provides new method for modulation of gluconeogenesis by altering EGR1 and/or DUSP4 activities.

Transcriptional targets of activated AMPK are necessary for its ability to repress hepatocyte glucose production. Transcriptional profiling of the AML12 and H4IIE hepatocyte cell lines treated with AICAR identified Early Growth Response factor 1 (EGR1) and Dual Specificity Phosphatase 4 (DUSP4) as two of these targets. Modulating the expression levels of either of these genes affected the ability of AICAR to repress both PEPCK and G6P activated transcription. In addition, siRNA-mediated knockdown of DUSP4 and EGR1 in Fao cells shows that these genes mediate at least part of the inhibition of glucose production by AICAR in Fao cells. EGR1 and DUSP 4 act sequentially to mediate the effect of AICAR. This is supported by the following data: (1) EGR1 protein expression is present 20 minutes after AICAR treatment followed by a DUSP4 increase at 2 hours; (2) chromatin immunoprecipitation experiments show that EGR1 binds to the DUSP4 promoter at 2 and 6 hours of treatment; and (3) siRNA mediated knockdown of EGR1 also knocks down expression of DUSP4. Additionally, EGR1 can potentiate AICAR-mediated repression of gluconeogenesis and DUSP4 over-expression is sufficient to repress gluconeogenesis. The fact that over-expression of DUSP4 can mimic the effect of AICAR suggests that it is the primary protein mediating the effect of EGR1 over-expression, although other EGR1 target genes may also make major contributions. Thus, the EGR1-DUSP4 pathway provides novel targets to modulate gluconeogenesis including, for example, in the context of dysfunction in hepatic glucose output in type 2 diabetes.

EGR1

The present invention contemplates that an increase in EGR1 activity can promote a reduction in gluconeogenesis. An increase in EGR1 activity can be achieved by increasing the activity of endogenous human EGR1 by, for example, increasing transcription or translation of endogenous human EGR1 in a human cell; by inhibiting degradation of the endogenous EGR1 transcript or protein; or by modifications that increase the specific activity of endogenous EGR1; or by increasing the activities of EGR1 confactors.

Increased Expression of Endogenous EGR1

Thus, in some embodiments, an increase in EGR1 activity can be achieved by increasing transcription or translation of endogenous human EGR1. This can be achieved by overexpression of transcription factors (e.g., CREB) that directly activates the transcription of EGR1. This can also be achieved by activating GM-CSF, IL-3, or other signaling pathways that directly or indirectly activate EGR1. See Kinane et al. (1994) *J Biol. Chem.*, 269(44):27503-9; and Lee et al. (1995) *J Biol. Chem.* 270(27):15979-15983, the teachings of which are hereby incorporated by reference. In addition, it has been reported that activation of extracellular signal-regulated protein kinase (ERK) triggers the biosynthesis of EGR1, and the tumor promoter 12-O-tetradecanoylphorbol-13-acetate (TPA) strongly upregulates EGR1 biosynthesis. See Bauer et al. (2005) *Arch Biochem Biophys.* 438(1):36-52. Epub 2005 Apr. 8, the teachings of which are hereby incorporated by reference.

Overexpression of Exogenous EGR1

EGR1 activity can also be increased by overexpression of an introduced nucleic acid encoding an EGR1 polypeptide. It is understood that an EGR1 polypeptide includes a polypeptide homologous or analogous to human EGR1 protein, and any polypeptide capable of binding to the sequence CGTGACCGGGAGC (SEQ ID NO:5) and of promoting transcription of human DUSP4. In many embodiments, an EGR1 polypeptide retains 60%, 65%, 70%, 75%, 80%, 85%, 90%, 95%, 97%, 99%, or more global sequence identity or similarity to the original human protein, and retains at least 50%, 60%, 70%, 80%, 90% or more of the biological function of the original protein. Sequence identity or similarity can be determined using various methods known in the art, such as Basic Local Alignment Tool (BLAST), the algorithm of Needleman et al. (1970) *J. Mol. Biol.* 48:444-453, the algorithm of Meyers et al. (1988) *Comput. Appl. Biosci.* 4:11-17, or dot matrix analysis.

Additional polypeptide(s) can be fused to the EGR1 polypeptide to facilitate its purification, detection, immobilization, folding, or targeting. The fused polypeptide(s) can also serve to increase the expression, solubility, or stability of the resulting protein. Other modifications, such as glycosylation, GPI anchor formation, or myristoylation, can also be introduced into a variant of the present invention.

A nucleic acid encoding a EGR1 polypeptide can be DNA, RNA, or a modified form thereof and may be optionally modified to increase its in vivo stability. Suitable modifications include, but are not limited to, the addition of flanking sequences at the 5' or 3' end, the use of phosphorothioate or 2-o-methyl instead of phosphodiesterase linkages in the backbone, and the inclusion of nontraditional bases such as inosine, queosine and wybutosine, as well as acetyl-, methyl-, thio- or other modified forms of adenine, cytidine, guanine, thymine and uridine.

Increased EGR1 Cofactor Activities and Other Modifications

Additionally, EGR1 activity can also be increased by increasing the activities of EGR1 cofactors. Cofactors of EGR1 have previously been reported. For example, Levkovitz et al. reported that c-Jun may act as a co-factor for EGR1 function. See, Levkovitz et al. (2002) *J. Neurosci.* 22:3845-3854, the teachings of which are hereby incorporated by reference. Zhang et al. reported that c/EBPβ or CREB may function as cofactors for EGR1. See, Zhang et al. (2002) *J. Lipid Res.*, 43:1477-1485, the teachings of which are hereby incorporated by reference.

Furthermore, EGR1 activity can be increased by any modifications to the EGR1 protein itself or other proteins in the relevant pathways that inhibit degradation of the EGR1 transcript or protein or increase the specific activity of EGR1.

Inhibition of EGR1 Activity

Alternatively, the present invention also contemplates methods of promoting gluconeogenesis by decreasing EGR1 activity. A decrease in EGR1 activity can be achieved by decreasing the activity of endogenous human EGR1 by, for example, providing an inhibitor of the human EGR1 gene or protein function. In particular, EGR1 gene function can be inhibited by interfering RNAs. The EGR1 protein function can be inhibited by a dominant-negative EGR1 protein. Since EGR1 regulates the transcription of a number of tumor suppressor genes, such as p53 and PTEN, the present invention contemplates inhibitors of EGR1 gene or protein function that have minimal effects on the transcription of tumor suppressor genes.

Inhibition of EGR1 by Interfering RNAs

The present invention features polynucleotides having antisense sequences for the EGR1 gene. An antisense molecule of the present invention can be complementary to a coding or non-coding region of the EGR1 gene. An antisense molecule can be complementary to the entire coding strand of the EGR1 gene or only a portion thereof. In many embodiments, the antisense molecules are oligonucleotides including, without limitation, about 10, 15, 20, 25, 30, 35, 40, 45, 50, or more nucleotide residues. The antisense molecule can be provided as an interfering RNA. The antisense molecule can also be provided by providing a DNA encoding an RNA inhibitor. The antisense molecules of the present invention can also comprise modified nucleotides to increase the biological stability of these molecules or the physical stability of the duplex formed between the antisense and sense polynucleotides.

In one embodiment, an antisense molecule of the present invention includes a nucleotide sequence that is complementary to a region of EGR1 mRNA. In another embodiment, an antisense molecule of the present invention is designed to have at least 95%, 96%, 97%, 98%, 99% or 100% sequence homology to a region in the mRNA of the EGR1 gene. In still another embodiment, an antisense molecule of the present invention is designed to be able to hybridize under stringent conditions to an mRNA region of the EGR1 gene. Typically, these probes or primers can hybridize under stringent conditions to the region from which they are derived, but not to the mRNAs or cDNAs that encode other genes.

"Stringent conditions" are at least as stringent as a condition selected from Table 1. In Table 1, hybridization is carried out under hybridization conditions (Hybridization Temperature and Buffer) for about four hours, followed by two 20-minute washes under the corresponding wash conditions (Wash Temp. and Buffer).

TABLE 1

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B^*$; 1xSSC | $T_B^*$; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D^*$; 1xSSC | $T_D^*$; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F^*$; 1xSSC | $T_F^*$; 1xSSC |
| G | DNA:DNA | >50 | 65° C.; 4xSSC -or- 42° C.; 4xSSC, 50% formamide | 65° C.; 1xSSC |
| H | DNA:DNA | <50 | $T_H^*$; 4xSSC | $T_H^*$; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J^*$; 4xSSC | $T_J^*$; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L^*$; 2xSSC | $T_L^*$; 2xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6(log$_{10}$Na$^+$) + 0.41(% G + C) − (600/N), where N is the number of bases in the hybrid, and Na$^+$ is the molar concentration of sodium ions in the hybridization buffer (Na$^+$ for 1xSSC = 0.165M).

The present invention further contemplates the use of RNA interference ("RNAi") to inhibit the expression of EGR1 in human cells or tissues. Any type of RNAi sequence can be used for the present invention. Non-limiting examples include short interfering RNA (siRNA) molecules or short hairpin RNA (shRNA). A variety of algorithms are available for RNAi sequence design. In one embodiment, the target sequences for siRNA include about 18, 19, 20 or more nucleotides. 2dT's can be added to the 3' end during siRNA synthesis, creating an "AA" overhang. Typically, the GC content of a target sequence is between 35% and 55%, and the sequence does not include any four consecutive A or T (i.e., AAAA or TTTT), three consecutive G or C (i.e., GGG or CCC), or seven "GC" in a row. More stringent criteria can also be employed. For instance, the GC content of a target sequence can be limited to between 45% and 55%, and any sequence having three consecutive identical bases (i.e., GGG, CCC, TTT, or AAA) or a palindrome sequence with 5 or more bases can be excluded. Furthermore, the target sequence can be selected to have low sequence homology to other variants or genes. The effectiveness of an RNAi molecule can be evaluated by introducing or expressing the RNAi sequence in a cell that expresses the EGR1 gene. A substantial change in the mRNA or protein level of EGR1 is indicative of the effectiveness of the RNAi molecule in inhibiting the expression of the EGR1 gene.

Dominant-Negative EGR1

The EGR1 protein function can be inhibited by a dominant-negative EGR1 construct. As used herein, "a dominant-negative EGR1" refers to any molecule capable of directly or indirectly inhibiting the activity of endogenous EGR1 protein. Typically, a dominant-negative EGR1 may be a protein. Exemplary dominant-negative EGR1 proteins are described in Stefano et al. "Up-regulation of tyrosine hydroxylase gene transcription by tetradecanoylphorbol acetate is mediated by the transcription factors Ets-like protein-1 (Elk-1) and Egr-1," (Mar. 3, 2006) [Epub ahead of print] *J Neurochem.*, the teachings of which are hereby incorporated by reference. Additional examples of dominant-negative EGR1 constructs are described in Wissam et al. (2005) *J. Biol. Chem.* 280: 9536-9546, the teachings of which are hereby incorporated by reference. A dominant-negative EGR1 may also be a nucleic acid, such as, for example, a nucleic acid including a EGR1 binding site.

DUSP4

Levels of gluconeogenesis can also be affected by modulating DUSP4 activity. The human DUSP4 gene sequence is provided in FIG. 9.

An increase in DUSP4 activity can promote a reduction in gluconeogenesis. An increase in DUSP4 activity can be achieved by increasing the activity of endogenous human DUSP4 by, for example, increasing transcription or translation of endogenous human DUSP4 in a human cell; by inhibiting degradation of the endogenous DUSP4 transcript or protein; or by modifications that increase the specific activity of endogenous DUSP4.

Increased Expression of Endogenous DUSP4

One method of promoting transcription of the endogenous DUSP4 gene is by increasing EGR1 activity as previously described. FIG. 10 is an alignment of a selected portion of the human and rat DUSP4 promoters. In the figure, the sequence corresponding to the EGR1 binding site is identified in bold-face type. The EGR1 binding site from the rat promoter is well conserved in the human promoter, as are the surrounding nucleotides. Thus, by providing a protein capable of i) binding the sequence CGTGACCGGGAGC (SEQ ID NO:5) and ii) promoting transcription, DUSP4 activity can be increased, promoting a reduction in gluconeogenesis.

Overexpression of Exogenous DUSP4

An increase in DUSP4 activity can also be achieved by overexpression of an introduced nucleic acid encoding a DUSP4 polypeptide or administration of a DUSP4 polypeptide in a form capable of entering the cell and reaching the cellular compartment housing kinase p38. In either case, the DUSP4 polypeptide normally includes at least the catalytic domain of the protein and may also include amino-terminal sequences, although these tend to be less well conserved among dual specificity phosphatases. It is understood that, much as the DUSP4 polypeptide can tolerate various deletions, it can also tolerate a variety of substitutions and additions without compromising its ability to act on kinase p38. In many embodiments, a DUSP4 polypeptide retains 60%, 65%, 70%, 75%, 80%, 85%, 90%, 95%, 97%, 99%, or more global sequence identity or similarity to the original human protein, and retains at least 50%, 60%, 70%, 80%, 90% or more of the biological function of the original protein. Sequence identity or similarity can be determined using various methods known in the art, such as Basic Local Alignment Tool (BLAST), the algorithm of Needleman et al. (1970) *J. Mol. Biol.* 48:444-453, the algorithm of Meyers et al. (1988) *Comput. Appl. Biosci.* 4:11-17, or dot matrix analysis.

An increase in DUSP4 activity can also be achieved by administering an isolated DUSP4 polypeptide capable of reaching a hepatocyte and dephosphorylating kinase p38. An isolated polypeptide (or polynucleotide) is substantially free from other polypeptides (or polynucleotides) or contains no more than an insignificant amount of contaminants that would interfere with its intended use. In many cases, a preparation of an isolated polypeptide (or polynucleotide) contains less than 80%, 70%, 60%, 50%, 40%, 30%, 20%, 10%, 5%, or 1% by weight of other polypeptides (or polynucleotides). An isolated variant or a polynucleotide encoding the same can be prepared using any method known in the art, including but not limited to, standard recombinant DNA technology, standard protein or nucleic acid isolation techniques, or chemical synthesis.

Additional polypeptide(s) can be fused to the DUSP4 polypeptide to facilitate its purification, detection, immobilization, or folding, targeting. The fused polypeptide(s) can also serve to increase the expression, solubility, stability, or targeting of the resulting protein. For example, a DUSP4 protein can be fused to a targeting domain to promote targeting to the liver and/or uptake into hepatocytes. The targeting domain can incorporate, for example, a ligand for a receptor expressed on hepatocytes, such as the class B, type I scavenger receptor (Graf et al. (1999) *J. Biol. Chem.* 274(17):12043-12048, the complete disclosure of which is incorporated herein by reference), the coxsackie and adenovirus receptor (Awasthi et al. (2004) *J. Virol.* 78(12):6431-6438, the complete disclosure of which is incorporated herein by reference), the asialoorosomucoid receptor, or the receptor for the malaria circumsporozoite protein (Ding et al. (1995) *J. Biol. Chem.* 270(8):3667-3676, the complete disclosure of which is incorporated herein by reference). The fused polypeptide can incorporate other portions capable of promoting the traversal of an administered protein across the plasma membrane, such as a viral TAT protein. Other modifications, such as glycosylation, GPI anchor formation, or myristoylation, can also be introduced.

Inhibition of DUSP4 by Interfering RNAs

The present invention features polynucleotides having antisense sequences for the DUSP4 gene. An antisense molecule of the present invention can be complementary to a coding or non-coding region of the DUSP4 gene. An antisense molecule can be complementary to the entire coding strand of the DUSP4 gene or only a portion thereof. In many embodiments, the antisense molecules are oligonucleotides including, without limitation, about 10, 15, 20, 25, 30, 35, 40, 45, 50, or more nucleotide residues. The antisense molecule can be provided as an interfering RNA. The antisense molecule can also be provided as a DNA encoding an RNA inhibitor. The antisense molecules of the present invention can also comprise modified nucleotides to increase the biological stability of these molecules or the physical stability of the duplex formed between the antisense and sense polynucleotides.

In one embodiment, an antisense molecule of the present invention includes a nucleotide sequence that is complementary to a region in the DUSP4 mRNA. In another embodiment, an antisense molecule of the present invention is designed to have at least 95%, 96%, 97%, 98%, 99% or 100% sequence homology to a region in the mRNA of the DUSP4 gene. In still another embodiment, an antisense molecule of the present invention is designed to be able to hybridize under stringent conditions to a region in the mRNA of the DUSP4 gene. Typically, these probes or primers can hybridize under stringent conditions to the region from which they are derived, but not to the mRNAs or cDNAs that encode other genes.

The present invention further contemplates the use of RNA interference ("RNAi") to inhibit the expression of DUSP4 in human cells or tissues. Any type of RNAi sequence can be used for the present invention. Non-limiting examples include short interfering RNA (siRNA) molecules, short hairpin RNA (shRNA), or microRNA. A variety of algorithms are available for RNAi sequence design. In one embodiment, the target sequences for siRNA include about 18, 19, 20 or more nucleotides. 2dT's can be added to the 3' end during siRNA synthesis, creating an "AA" overhang. Typically, the GC content of a target sequence is between 35% and 55%, and the sequence does not include any four consecutive A or T (i.e., AAAA or TTTT), three consecutive G or C (i.e., GGG or CCC), or seven "GC" in a row. More stringent criteria can also be employed. For instance, the GC content of a target sequence can be limited to between 45% and 55%, and any sequence having three consecutive identical bases (i.e., GGG, CCC, TTT, or AAA) or a palindrome sequence with 5 or more bases can be excluded. Furthermore, the target sequence can be selected to have low sequence homology to other variants or genes. The effectiveness of an RNAi molecule can be evaluated by introducing or expressing the RNAi sequence in a cell that expresses the DUSP4 gene. A substantial change in the mRNA or protein level of DUSP4 is indicative of the effectiveness of the RNAi molecule in inhibiting the expression of the DUSP4 gene.

Dominant-Negative DUSP4

DUSP4 protein function can be inhibited by a dominant-negative DUSP4. As used herein, "a dominant-negative DUSP4" refers to any molecule capable of directly or indirectly inhibiting the activity of endogenous DUSP4 protein. Typically, a dominant-negative DUSP4 may be a protein. For example, a dominant-negative DUSP4 could be constructed in a manner analogous to the construction of dominant-negative DUSP1, as described in. A dominant negative DUSP4 may also be a nucleic acid, such as, for example, a nucleic acid selected for binding to DUSP4.

Vectors

A nucleic acid encoding an EGR1 or DUSP4 polypeptide can be DNA, RNA, or a modified form thereof and is optionally modified to increase its in vivo stability. Suitable modifications include, but are not limited to, the addition of flanking sequences at the 5' or 3' end, the use of phosphorothioate or 2-o-methyl instead of phosphodiesterase linkages in the backbone, and the inclusion of nontraditional bases such as inosine, queosine and wybutosine, as well as acetyl-, methyl-, thio- or other modified forms of adenine, cytidine, guanine, thymine and uridine.

A nucleic acid encoding an EGR1 or DUSP4 polypeptide can be incorporated into an expression vector that also includes 5' or 3' untranslated regulatory sequences. The design of expression vectors depends on such factors as the choice of the host cells and the desired expression levels. Selection of promoters, enhancers, selectable markers, or other elements for an expression vector is a matter of routine design within the level of ordinary skill in the art. Many such elements are described in the literature and are available through commercial suppliers. The expression vector can be a virus, such as adenovirus or other viruses useful for nucleic acid administration in vitro or in vivo.

Hepatocyte Targeting

To facilitate targeting of the compositions of the invention to the liver and/or uptake into hepatocytes, the compositions can incorporate a targeting domain or a vector that functions as a ligand for a receptor expressed on hepatocytes, such as the class B, type I scavenger receptor (Graf et al. (1999) *J. Biol. Chem.* 274(17):12043-12048, the complete disclosure of which is incorporated herein by reference), the coxsackie and adenovirus receptor (Awasthi et al. (2004) *J. Virol.* 78(12):6431-6438, the complete disclosure of which is incorporated herein by reference), the asialoorosomucoid receptor, or the receptor for the malaria circumsporozoite protein (Ding et al. (1995) *J. Biol. Chem.* 270(8):3667-3676, the complete disclosure of which is incorporated herein by reference). For example, an EGR1 or DUSP4 polypeptide can be expressed as a fusion protein incorporating such a targeting domain, or another portion capable of promoting the traversal of an administered protein across the plasma membrane, such as a viral TAT protein. Other modifications, such as glycosylation, GPI anchor formation, or myristoylation, can also be introduced.

Administration

A composition of the present invention can be formulated to be compatible with its intended route of administration. Non-limiting examples of routes of administration include parenteral, intravenous, intradermal, subcutaneous, oral, inhalation, transdermal, rectal, transmucosal, topical, and systemic administration. The administration can also be carried out by using implants.

A pharmaceutical composition of the present invention typically includes a pharmaceutically acceptable carrier and a therapeutically or prophylactically effective amount of a gluconeogenesis modulator. A gluconeogenesis modulator can be used either individually or in combination with other gluconeogenesis modulators. The use of carrier media and agents for pharmaceutically active substances is well-known in the art. A pharmaceutical composition of the present invention can be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers. In one embodiment, the pharmaceutical compositions of the present invention are formulated and used as foams. Pharmaceutical foams include formulations such as emulsions, microemulsions, creams, jellies and liposomes. While basically similar in nature, these formulations vary in the components and the consistency of the final product. The preparation of such compositions and formulations is generally known to those skilled in the pharmaceutical and formulation arts and can be readily applied to the formulation of the compositions of the present invention.

It should be understood that the above-described embodiments and the following examples are given by way of illustration, not limitation. Various changes and modifications within the scope of the present invention will become apparent to those skilled in the art from the present description.

EXAMPLES

Example 1

Identification of Transcripts Significantly Regulated by AICAR in Hepatocytes

In order to identify transcriptional targets of activated AMPK in hepatocytes, with a goal of further understanding its role in negatively regulating gluconeogenesis, the mouse hepatoma cell line AML12 was treated with 500 µM AICAR for either 2, 6, or 24 hours in triplicate. AML12 cells were maintained in DMEM/F12 medium containing 10% FCS, 5 mg/ml insulin, 5 mg/ml transferrin, 5 ng/ml selenium and 40 ng/ml dexamethasone.

Double-stranded cDNA was synthesized starting with 5 µg of total RNA from the cells using the SuperScript System (Invitrogen, Carlsbad, Calif.). The cDNA was purified by filtration through Multiscreen filter plate (Millipore), and transcribed in vitro using T7 RNA polymerase (Epicentre, Madison, Wis.) and biotinylated nucleotides (Perkin-Elmer, Boston, Mass.). Hybridization buffer containing the spike pool reagent was added to each of the fragmented cRNA mixtures and each sample was hybridized to the Mouse Genome 430 2.0 array (MAE430) or Rat Genome 230 2.0 array (RAE230) (Affymetrix, Santa Clara) at 45° C. for 18 hours as recommended by the manufacturer. The hybridized chips were washed and stained using Affymetrix Fluidics Station 450 and the EukGE-WS2v4_450 protocol as recommended by the manufacturer. The staining was performed using streptavidin-phycoerythrin conjugate (SAPE; Molecular Probes, Eugene, Oreg.), followed by biotinylated antibody against streptavidin (Vector Laboratories, Burlingame, Calif.), and then SAPE. The chips were scanned using an Affymetrix Genechip Scanner and .cel files were generated with Affymetrix Microarray Suite 5.0 (MAS 5.0) software.

Using normalized data, after removing lowly expressed genes, we performed ANOVA analysis. Qualifiers that were induced or repressed in a statistically significant ($p \leq 0.05$) way at all three time points between AICAR and vehicle treated samples we identified. The expression patterns of these 43 qualifiers are represented in FIG. 1. Among the qualifiers that increased with greatest significance upon AICAR treatment were Dual Specificity Phosphatase 4 (DUSP4) and the zinc finger transcription factor Early Growth Response 1 (EGR1). The normalized frequency of each of these qualifiers at each time point with and without AICAR treatment is also shown in FIG. 1. DUSP4 message increased 4, 6, and 5 fold over the time course relative to untreated controls with the highest individual expression occurring at 6 hours of treatment. EGR1 increased 3 fold at 2 and 6 hours of treatment relative to control and 2 fold at 24 hours.

Very few genes regulated by AICAR have previously been reported. Many of the genes are down-regulated. Interestingly, we find preponderance of up-regulated genes in our profiling experiment. Additionally, AMPK has generally been found to exert effects through inhibition of transcription by factors such as ChREBP, HNF-4α, and p300, and through inhibition of translation by TSC2 and mTOR, yet here we show an acute and immediate induction of EGR1 and DUSP4 that appears to be necessary for downstream effects (Hong et al. (2003) *J. Biol. Chem.* 278:27495-27501; Kawaguchi et al. (2001) *Proc. Natl. Acad. Sci U.S.A.* 98:13710-13715; Yang et al. (2001) *J. Biol. Chem.* 276:38341-38344; Inoki et al. (2003) *Cell* 115:577-590). Many of the known genes are regulated later (e.g. HNF4 protein levels decrease after 6 h of treatment) as well. It is possible that the induction of EGR1 is so strong as to overcome other inhibitory effects of AMPK activation, and it has been shown that AMPK activation down-regulates nuclear hormone receptor-driven transcription while preserving p300 mediated activation of non-nuclear receptor transcription factors, of which EGR1 is one (Leff (2003) *Biochem. Soc. Trans.* 31:224-227).

AICAR treatment was also performed over the time course period on H4IIE rat hepatoma cells cultured in DMEM containing 5% FCS. Total RNA was isolated from these cells and hybridized on the RAE430 2.0 array and analyzed in the same manner as the AML12 cells. The number of qualifiers changing was much more robust with treatment of these cells. Using similar filtering conditions as described above, the expression of 54 qualifiers were induced or repressed in a statistically significant ($p \leq 1 \times 10^{-4}$) manner at every time point when comparing AICAR versus vehicle treated samples.

Figure 2:
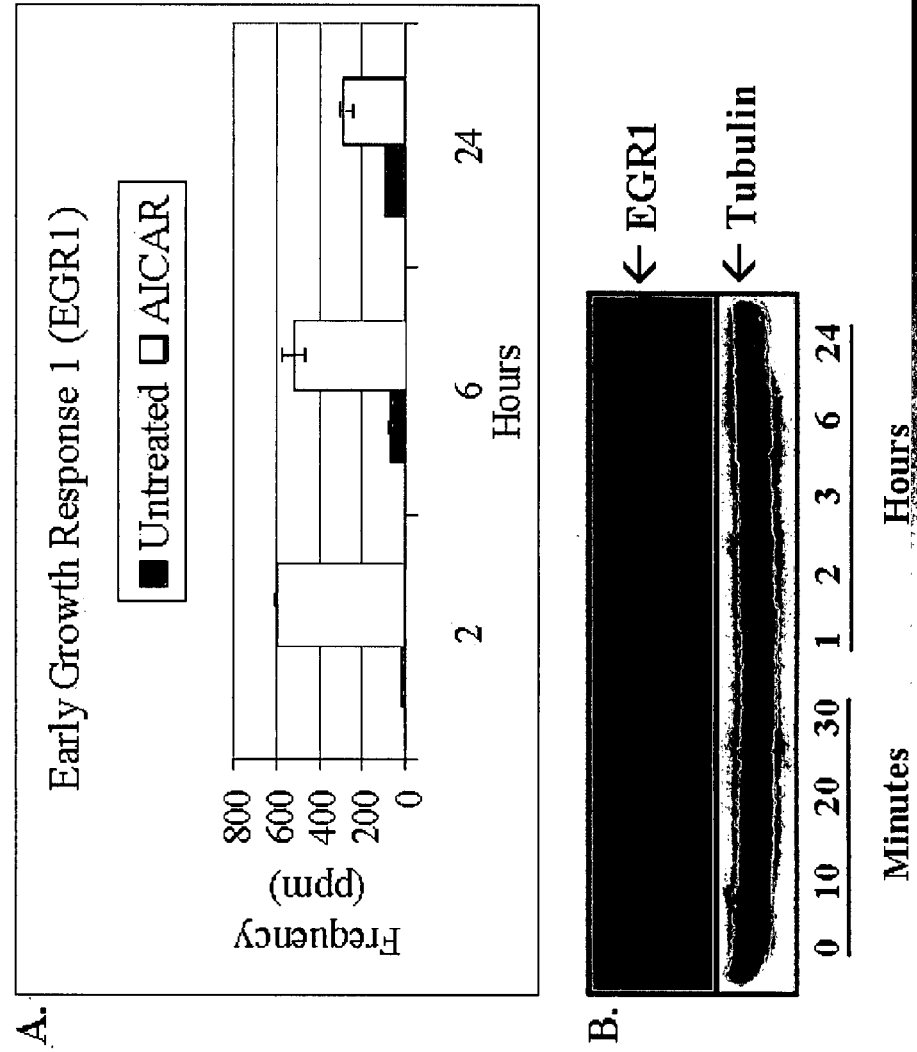
FIG. 2 schematically depicts the induction of EGR1 by AICAR in H4IIE hepatocytes. Panel A illustrates the mean expression ±STD of EGR1 (qualifier #1368321_at) on the RAE230 2.0 array following treatment with AICAR for the indicated time. Panel B is a Western blot of EGR1 following AICAR treatment for the indicated times. The anti-tubulin blot is a loading control.

The normalized frequency of EGR1 over the time course of this experiment is shown in FIG. 2A. Expression increased 6 fold, 5 fold, and 3 fold relative to control over the time course. In order to further investigate the time course of EGR1 induction with AICAR treatment an anti-EGR1 Western blot was performed at time points ranging from 10 minutes of treatment up to 24 hours.

As shown in FIG. 2B, EGR1 expression increases as early as 20 minutes of treatment, increasing up to 6 hours, and slightly decreasing by 24 hours. Lysates were prepared with a buffer containing 20 mM Tris (pH 7.5), 150 mM NaCl, 1 mM EDTA, 1 mM EGTA, 1% Triton X-100, 2.5 mM sodium pyrophosphate, 1 mM β-glycerophosphate, 1 mM sodium vanadate, and 1 μg of leupeptin/ml. 20 μg of lysate for each sample was run on NuPAGE 10% polyacrylamide bis/tris gels (Invitrogen) and transferred to PVDF membrane. Following blocking with 5% milk in TBS, anti-EGR1 (SC-110, Santa Cruz) at 1:1000 or anti alpha-tubulin (Abcam) at 1:2000 was blotted in TBS with 0.1% Tween. Goat anti-mouse HRP (Jackson Immuno-Research) was used at 1:5000 and blots were visualized by using enhanced chemiluminescence (NEN).

Figure 3:
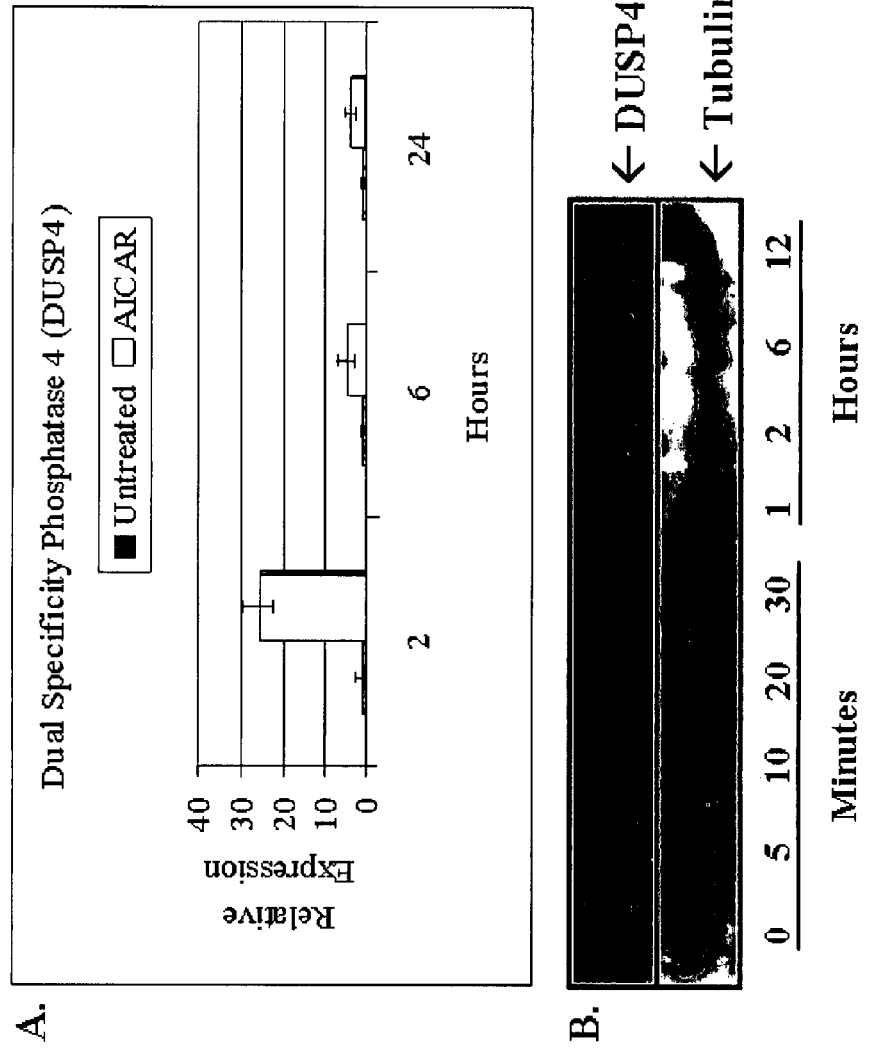
FIG. 3 schematically demonstrates the induction of DUSP4 by AICAR in H4IIE hepatocytes. Panel A depicts the relative expression of DUSP4 following AICAR treatment for the indicated times as determined by TaqMan real-time PCR with Assay on Demand primer set (Applied Biosystems). Panel B is a Western blot of DUSP4 following AICAR treatment for the indicated times. As in FIG. 2, the anti-tubulin blot is a loading control.

DUSP4 expression also increased with AICAR treatment in H4IIE cells. FIG. 3A shows the results of a TaqMan real time PCR analysis of DUSP4 mRNA levels following 2, 6, and 24 hours of treatment. Taqman was utilized since the DUSP4 probe set on the RAE430 2.0 array was not as sensitive as the DUSP4 set on the MOE430 2.0 array. DUSP4 message increased 20 fold at 2 hours of treatment, and 4 fold at both 6 and 24 hours of treatment. Western blot analysis using anti-DUSP4 (SC-1200, Santa Cruz) at a dilution of 1:300 (FIG. 3B) showed an increase of DUSP4 protein at 2 and 6 hours with a decrease to more basal levels at 12 hours.

Figure 4:
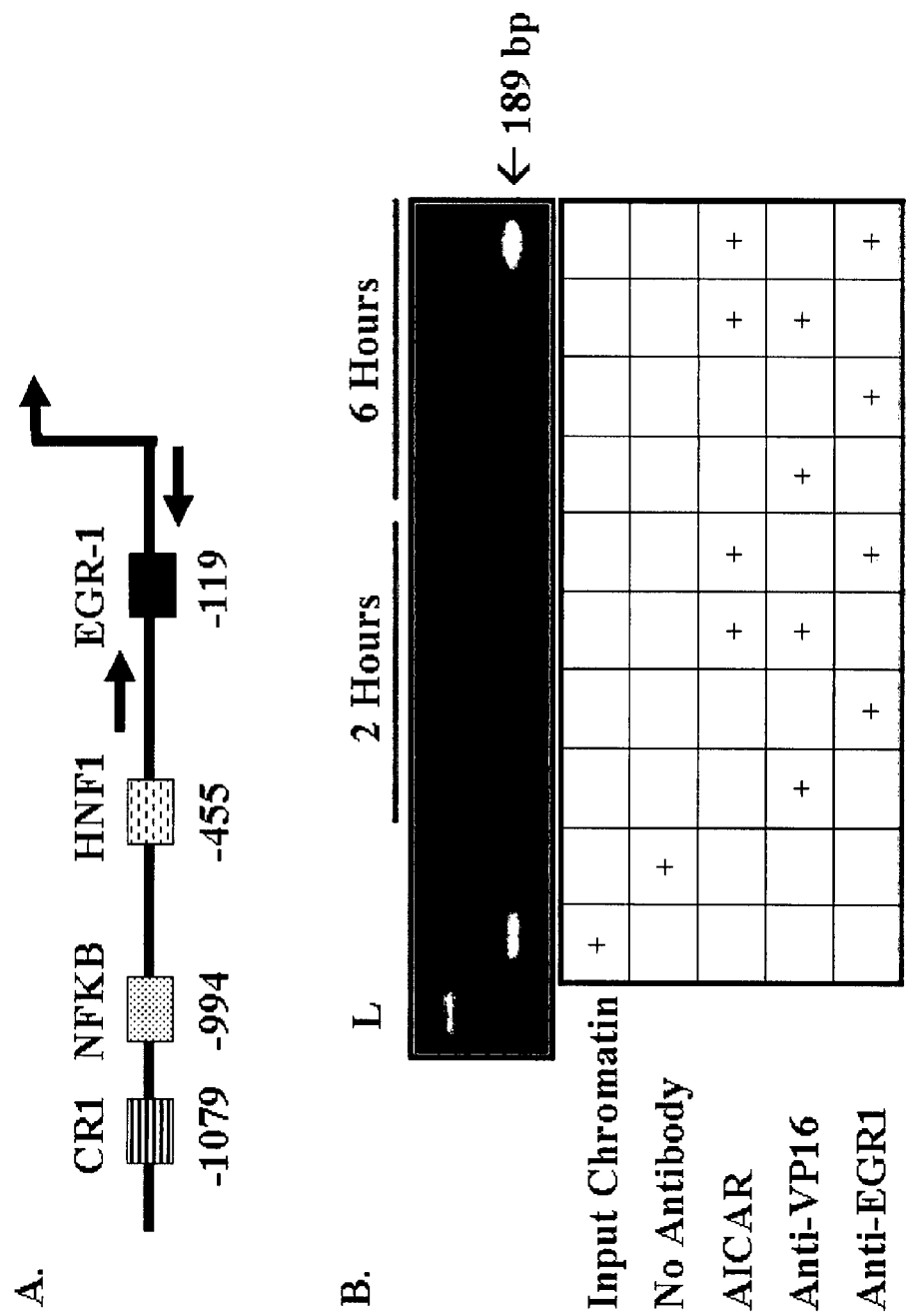
FIG. 4 schematically describes EGR1 binding to the rat DUSP4 promoter following treatment with AICAR. Panel A is a schematic of the rat DUSP4 promoter including putative binding sites for additional transcription factors. Arrows indicate sites of primers used for chromatin immunoprecipitation assay (−72 to −261 bp from the transcriptional start site). Panel B is an ethidium bromide-stained agarose gel showing results of PCR with the indicated primers in the DUSP4 promoter following chromatin immunoprecipitation with either anti-EGR1 or anti-VP16 as a negative control after H4IIE treatment with AICAR for the indicated time.

DUSP4 was previously identified as a transcriptional target of the immediate early transcription factor EGR1 in response to gonadotropin releasing hormone in pituitary cells (Zhang et al. (2001) *J. Biol. Chem.* 276:45604-45613). Upon treatment with GnRH, EGR1 bound and activated the DUSP4 promoter. In order to test whether EGR1 bound the DUSP4 promoter in AICAR treated H4IIE cells, chromatin immunoprecipitation experiments were performed. FIG. 4A shows a schematic of the DUSP4 promoter including the reported EGR1 site and putative binding sites of other transcription factors. The EGR1 site identified as a response element during GnRH signaling is located 119 base pairs upstream of the transcriptional start site. Primers were designed to amplify this site and PCR was performed on DNA following immunoprecipitation of EGR1 protein/DNA complexes after AICAR treatment for either 2 or 6 hours as described below.

To cross-link protein and DNA, formaldehyde was added at a 1% (vol/vol) concentration to H4IIE cells in a 100 mm dish. Fixation proceeded for 10 min at room temperature with gentle shaking and was stopped with the addition of glycine to a final concentration of 0.125M, and then the mixture was incubated at room temperature for 5 min. The cells were then washed twice with cold phosphate-buffered saline (PBS), harvested, and washed once with PBS containing PMSF. The cell pellet was lysed with immunoprecipitation assay lysis buffer (150 mM NaCl, 1% NP-40, 0.5% deoxycholate, 0.1% sodium dodecyl sulfate [SDS], 50 mM Tris [pH 8], 5 mM EDTA and protease inhibitors [1 mM PMSF, 10 μg of aprotinin/ml, 10 μg of leupeptin/ml]) and incubated on ice for 10 min. The resulting lysate was sonicated to give chromatin of an average length of 600 to 1,000 bp. The lysate was then microcentrifuged at 14,000 rpm for 10 min at 4° C. The lysate was then precleared with 50 μl of protein A beads (IPA 400; Repligen) for 15 min. Immunoprecipitations were performed overnight with 2 μg of antibody in a total volume of 500 μl at 4° C. 50 microliters of protein A beads were then added to the lysates and incubated for 30 min at 4° C. The beads were then washed twice with IP dilution buffer (2 mM EDTA, 50 mM Tris-Cl [pH 8.0]), and 4 times with IP wash buffer (100 mM Tris-Cl [pH 8.0], 500 mM LiCl, 1% NP-40, 1% deoxycholic acid). The immune complexes were eluted twice in 200 μl of elution buffer (50 mM NaHCO3, 1% SDS) for 15 min. A 1 μl aliquot of high-concentration RNase was added, and the NaCl concentration was adjusted to 0.3M. Samples were then incubated at 67° C. for 5 h to reverse cross-links. Two volumes of ethanol were added for overnight precipitation at −20° C. The resulting pellets were collected, air dried, and resuspended in 100 μl of TE. Twenty-five microliters of 5× PK buffer (50 mM Tris-Cl [pH 7.5], 25 mM EDTA, 1.25% SDS) was added with 1 μl of proteinase K. The samples were digested at 45° C. for 2 h. 175 microliters of TE were then added. The DNA was purified by standard phenol-chloroform and chloroform extractions and precipitated with 0.3M NaCl, 5 μg of glycogen carrier, and 2 volumes of ethanol for overnight precipitation at −20° C. The purified DNA was resuspended in 20 μl of water. A 5 μl aliquot was analyzed by PCR with Vent polymerase (NEB). For the rat DUSP4 promoter, the sequence to be amplified resides at positions −72 to −264. The PCR primer sequences were

```
5'-GGCGGCTCCATTCACAAAGTCCG -3'     (SEQ ID NO:6)
and

5'-CCGACTCTTGAATGGAGCGCCG -3'.     (SEQ ID NO:7)
```

As shown in FIG. 4B, only upon AICAR treatment and immunoprecipitation with anti-EGR1 antibodies (not anti-VP16) was the EGR1 site amplified, as identified by the presence of a 189 bp PCR product. These results show that both EGR1 and DUSP4 are induced within 2 hours of AICAR treatment (EGR1 within 20 minutes), and that EGR1 occupies an element of the DUSP4 promoter previously shown to be necessary for its activation by GnRH.

Example 2

EGR1 and DUSP4 Inhibit Gluconeogenic Gene Transcription

Activation of AMPK via AICAR inhibits hepatic gluconeogenesis through inhibition of the transcription of the rate limiting enzymes phosphoenolpyruvate carboxykinase (PEPCK) and glucose-6-phosphatase (G6P) (Lochhead et al. (2000) *Diabetes* 49:896-903). Reporter assays were utilized to determine if EGR1 and DUSP4 are effectors of AICAR mediated inhibition of PEPCK and G6P.

The rat PEPCK promoter (−548 to +73) was amplified from rat genomic DNA using primers 5'-GCCTCGAGCTC-GAGTCCAGCAGACACCTAGTGGG-3' (SEQ ID NO:8) and 5'-GCAAGCTTAAGCTTTCTCGCCGGATTTC-CCCTGTTC-3' (SEQ ID NO:9) (Xu et al. (2003)) *J. Biol. Chem.* 278:30187-30192). The human G6P promoter (−1227 to +57) was amplified from human genomic DNA using primers: 5'-GCCTCGAGCTCGAGTGAGCTCAGGAAT-TCAAGACC-3' (SEQ ID NO:10) and 5'-GCAAGCT-TAAGCTTAGATGTCAGCAGAGCCCTTGC-3' (SEQ ID NO:11). The promoters were subsequently cloned into XhoI and HindIII sites of pSEAP-BASIC vector (Clontech).

H4IIE cells were seeded in 24-well plates and transfected at 90% confluence using Tfx-50 Reagent (Promega). 0.9 μg of each SEAP reporter and 0.2 μg of pCMV-β-gal (BD Biosciences) were included. 0.4 μg of pCMV-XL5-human-DUSP4 (NM_001394, Origene) or pCMV-Sport6-human EGR1 (BC073983, Open Biosystems), or pMEV2HA-P38-WT and P38-EE (Biomyx), or empty pCMV-Sport6 were included. SiGenome Smartpool reagents were included at 25 nm. 24 hours after transfection cells were fasted for 5 hours in DMEM with 0.5% FBS followed by treatment with 200 ul of DMEM with 0.1% FBS with 100 μM cAMP (Calbiochem) and dexamethasone (Sigma) and/or 500 μM AICAR for 3 hours. 60 μl of the media was utilized for the SEAP assay (Great EscAPe SEAP Kit, BD Biosciences) and cell lysate was used for β-gal assay (Luminescent β-galactosidase detection kit, BD Biosciences).

Figure 5:
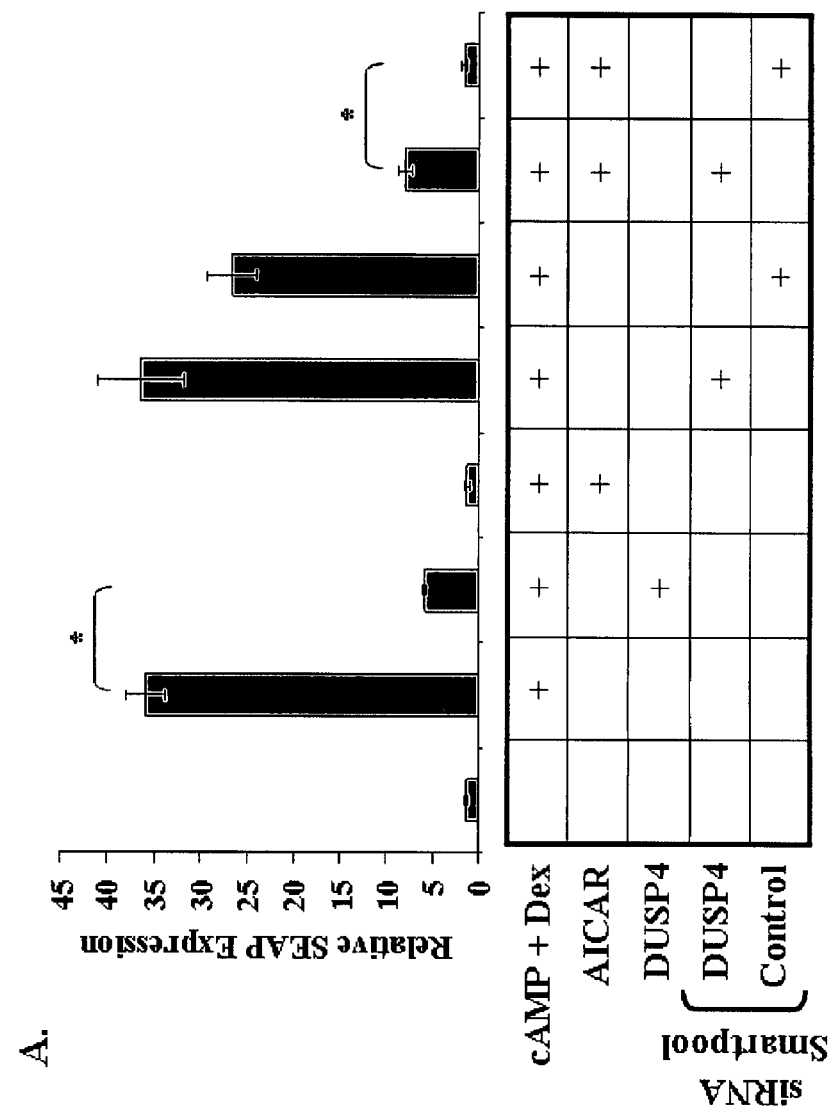
FIG. 5 schematically depicts the effects of EGR1 and DUSP4 expression levels on PEPCK promoter activity. For the experiments shown in panels A and B, H4IIE hepatocytes were transfected with the PEPCK-SEAP reporter plasmid and either DUSP4 or EGR1 expression plasmids or DUSP4 or EGR1 siRNA Smartpools. 24 hours after transfection the media were changed to 0.5%FBS/DMEM for 5 hours. The media were then changed to 0.1% FBS/DMEM with cAMP and dexamethasone with or without 500 µM AICAR for 16 hours and SEAP activity in the media was determined. Panel A depicts the effects of EGR1 modulation on PEPCK promoter activity; panel B depicts the effects of DUSP4 modulation on PEPCK promoter activity. Panel C demonstrates that exogenous expression of EGR1 that coincides with AICAR treatment affects PEPCK promoter activity. H4IIE hepatocytes were treated as in A and B but treated with either 100 µM or 500 µM AICAR on day 3. The asterisk indicates key changes between samples. P-values of all changes are ≦0.01 as determined by T-test.
Figure 5:
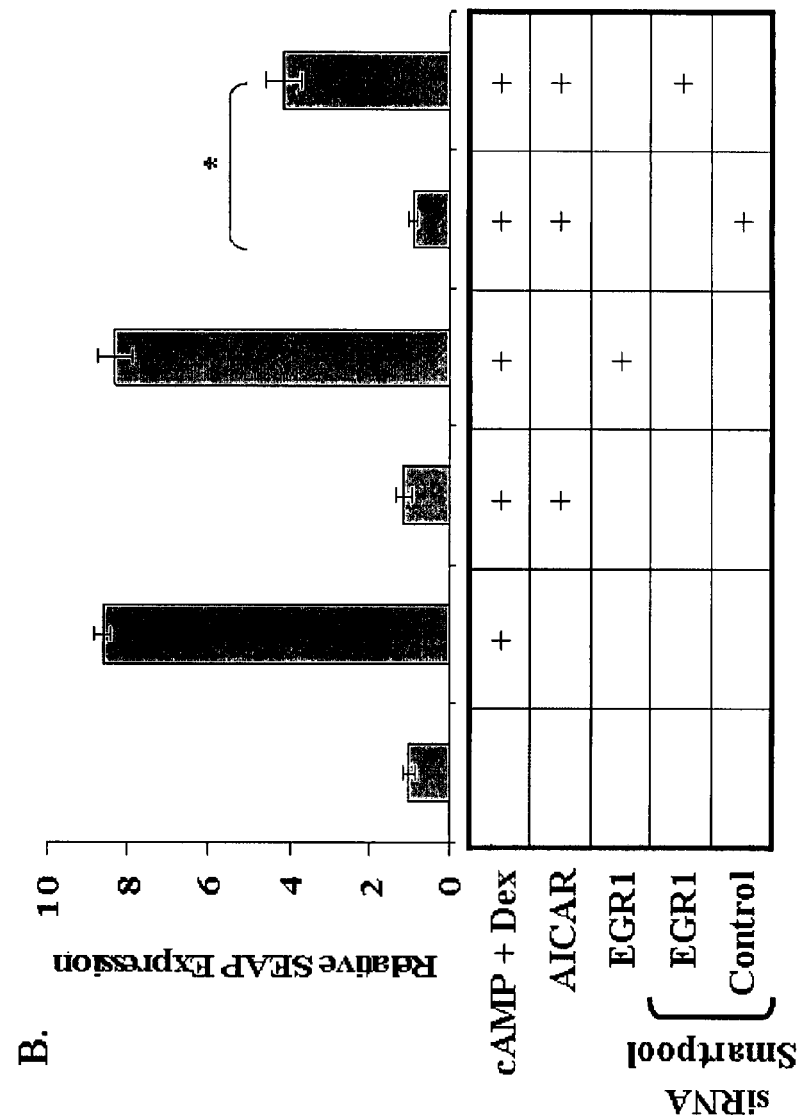
Figure 5:
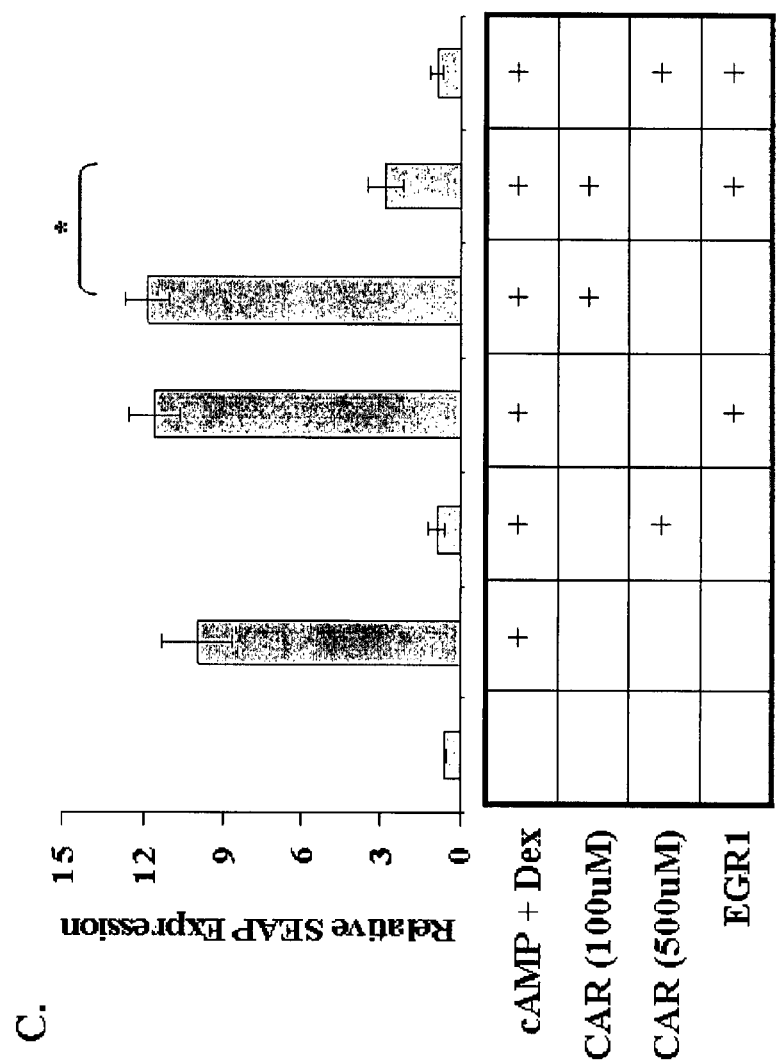

As has been previously reported, we found that, treatment of H4IIE cells with 500 μM AICAR inhibits the cAMP and dexamethasone-induced activation of the PEPCK promoter (FIG. 5A). In the figure, data are presented as relative SEAP activity with β-gal activity as a transfection control. Interestingly, transfection of H4IIE cells with DUSP4 expression vectors inhibited the cAMP and dexamethasone activation of the PEPCK promoter almost as potently as AICAR (from approximately 36 fold inhibition with AICAR to 6 fold with DUSP4 (p≦0.01)), suggesting that DUSP4 could mediate the effects of AICAR on PEPCK transcription. Further elucidating the role of DUSP4 in AMPK-mediated gluconeogenic inhibition, transfection of a DUSP4 siRNA Smartpool (a mix of 4 individual DUSP4-targeting siRNA molecules) impaired the ability of AICAR to completely inhibit PEPCK transcription (FIG. 5A). The sequences of the siRNA molecules include GAUCACGGCUCUACUGAAU (SEQ ID NO:1); CAAAUGAGUCCUGGAUCA (SEQ ID NO:2); GGACA-UUACCAGUACAAGU (SEQ ID NO:3); and GUGAACGUGCGCUGCAAUA (SEQ ID NO:4). A control Smartpool of non-targeting siRNA had an insignificant effect on the ability of AICAR to repress the activation by cAMP and dexamethasone. Similarly, addition of siRNA had an insignificant effect on the activation of PEPCK by cAMP and dexamethasone without AICAR. Thus, DUSP4 mediates at least part of the effect of AICAR on PEPCK transcription.

FIG. 5B shows the results of similar experiments upon modulating the levels of EGR1. Unlike DUSP4, transfection of exogenous EGR1 had no effect on the activation of PEPCK-SEAP. However, when EGR1 was transfected in the presence of a low AICAR concentration (100 μM), which by itself was not sufficient to inhibit PEPCK activation (FIG. 5C), PEPCK transcription was significantly reduced from 12 fold to 3 fold. Thus, EGR1 can potentiate the effects of AICAR on PEPCK transcription. It is possible that, in addition to inducing EGR1 transcription, AMPK activation also results in a modification to EGR1, such as phosphorylation, which is required for EGR1 activity. Alternatively, AMPK could also activate a co-factor necessary for EGR1 mediated transcription, although the expression of the repressors of EGR1 transcription NAB-1 or 2 did not change in our experiments (data not shown). It is interesting to note that EGR1 over-expression alone is also unable to modulate other assays (e.g. apoptosis) known to be dependent on EGR1, and co-factor requirements for EGR1 function have been suggested previously (Levkovitz et al. (2002) *J. Neurosci.* 22:3845-3854).

Depletion of EGR1 via siRNA smartpool partially abrogated the ability of AICAR to inhibit the PEPCK promoter (FIG. 5B). While in this set of experiments cAMP and dexamethasone activated the PEPCK reporter 13 fold, siRNA-mediated knockdown of EGR1 resulted in a 6-fold activation by cAMP and dexamethasone in the presence of AICAR, whereas AICAR fully repressed the activation when control siRNA were included. These reporter assays show that the induction of EGR1 and DUSP4 by AICAR is necessary for its ability to fully inhibit the PEPCK promoter. Similar experiments, over-expressing and depleting DUSP4 and EGR1, were performed using the G6P promoter, and yielded similar results (data not shown), suggesting that modulation by DUSP4 and EGR1 is not specific to the PEPCK promoter.

Example 3

Depletion of DUSP4 and EGR1 Abrogates the Ability of AICAR to Inhibit Glucose Production Transfection of Fao hepatoma cells with DUSP4 and EGR1 siRNA Smartpools resulted in a 60 and 70% reduction in their relative basal expression respectively (data not shown) as determined by Taqman. RNA was isolated and purified using RNeasy kits (Qiagen) according to manufacturer's instructions. mRNA levels were measured by TaqMan Real-time quantitative PCR using Assay-on-Demand Taqman reagents (Applied Biosystems). Taqman was performed in an ABI PRISM 7000 Sequence Detection System (PE Applied Biosystems) and the data were analyzed according to the manufacturer's instructions.

Figure 6:
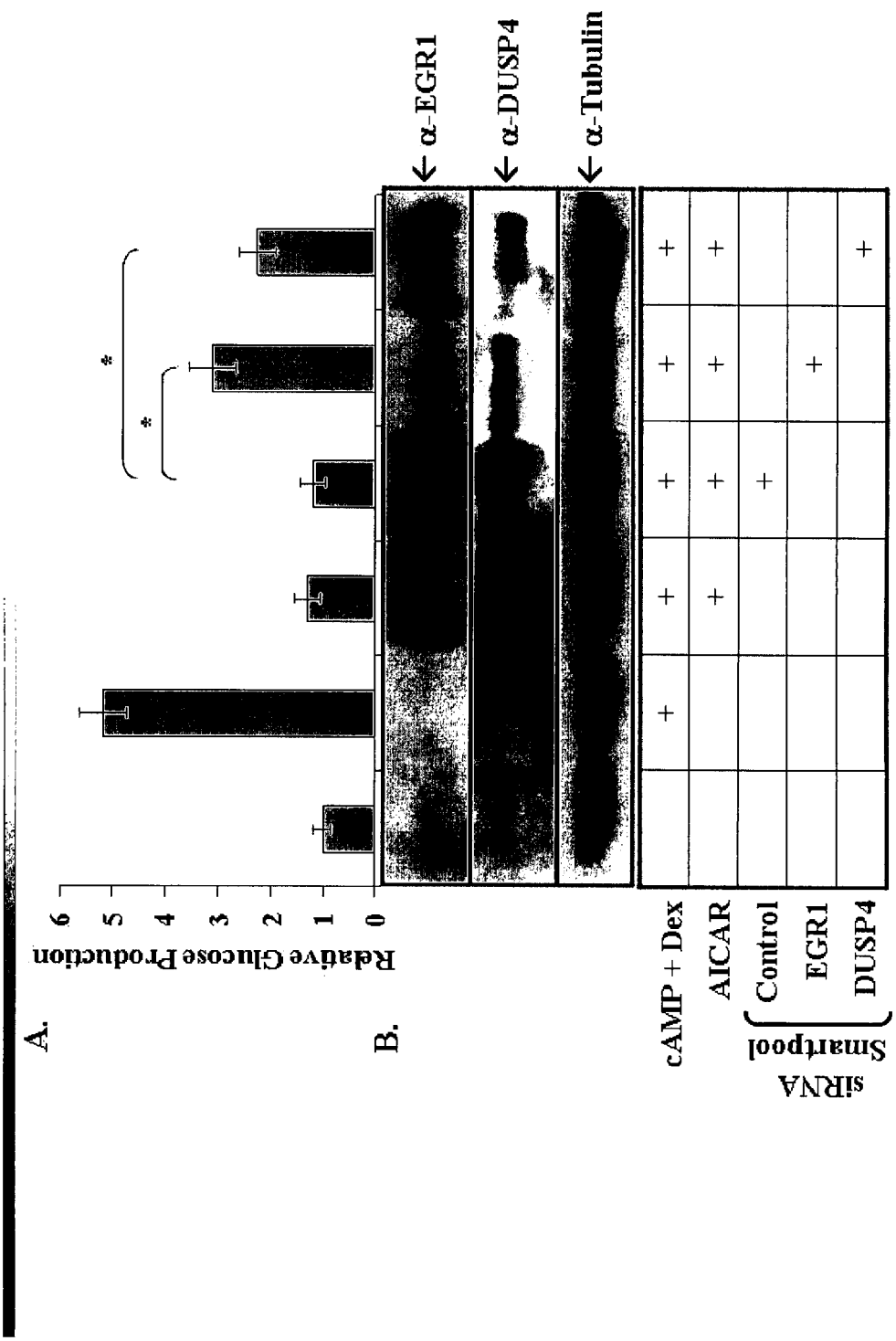
FIG. 6 demonstrates that depletion of EGR1 or DUSP4 attenuates the inhibition of glucose production by AICAR in Fao hepatoma cells. For the experiment shown in panel A, Fao cells were transfected with either EGR1 or DUSP4 siRNA Smartpools. 24 hours after transfection the cells were incubated in RPMI1640/0.5% BSA alone or with cAMP plus dexamethasone, or cAMP plus dexamethasone with 500 µM AICAR overnight. The cells were then cultured with phenol-red and glucose free RPMI1640 with 20 mM lactate and 2mM pyruvate. After 3 hours the media was collected and glucose output was determined. The data are presented as relative glucose production with the untreated transfected cells' glucose output set as 1. The asterisk indicates key changes between samples. P-values of all changes are ≦0.01 as determined by T-test. Panel B contains Western blots of EGR1 and DUSP4 or representative samples from the glucose production assay following transfection with the indicated siRNA Smartpools. The tubulin blot is included as a loading control.

FIG. 6 shows the results of glucose production assays in Fao cells upon reduction of EGR1 and DUSP4 by siRNA Smartpool transfection.

1 million Fao cells cultured in RPMI1640 with 10% FCS were transfected with siGenome SMARTpool reagents for EGR1 (#M-100247-00), DUSP4 (#M-098966-00), or siCONTROL Non-Targeting siRNA (Dharmacon) using Optifect (Invitrogen) at 25 nM final concentration. 24 hours after transfection cells were washed once with RPMI1640 and incubated in RPMI1640 containing 0.5% BSA, 1 μM dexamethasone (Sigma # D1881) and 1 mM cAMP (CalBiochem #28745) for 16 hours with and without 500 μM AICAR. Cells were then incubated in 0.35 ml (per well) of phenol red-free, glucose-free DMEM containing 2 mM pyruvate and 20 mM lactate containing dexamethasone and cAMP with or without AICAR as indicated in the figure legend. Medium was collected 5 hours later and subjected to glucose measurement using the Amplex® Red Glucose/Glucose Oxidase Assay Kit (Molecular Probes). Cells were lysed and protein concentration was determined. The glucose output rate was normalized by cellular protein concentration and expressed as µg glucose/mg protein/5 hr. Untreated samples' output was set to 1 and the data were presented as glucose output relative to the untreated samples.

The inclusion of DUSP4 and EGR1 siRNA Smartpools resulted in an abrogation of the ability of AICAR to inhibit glucose production. cAMP plus dexamethasone increased the glucose output of the Fao cells by 5 fold following 16 hours of starvation, which was inhibited by 500 µM AICAR to within 30% of untreated levels. Transfection of untargeted Smartpool siRNA had no effect on the ability of AICAR to inhibit glucose production. However, inclusion of the EGR1 siRNA Smartpool inhibited the AICAR mediated repression by 50%, which still resulted in a 3-fold increase in glucose production in the presence of AICAR. DUSP4 also inhibited, but to a lesser degree, allowing glucose production to increase just over 2 fold in the presence of 500 µM AICAR. These results are statistically significant with a student's T test value of $p \leq 0.01$. The Western blots of FIG. 5B show that the transfection of the DUSP4 siRNA resulted in a significant reduction of DUSP4 expression in the AICAR treated Fao cells. Interestingly, transfection of siRNA targeting EGR1 caused a reduction of both EGR1 protein induction as well as DUSP4 protein. This further suggests that EGR1 activates DUSP4 transcription following AMPK activation with AICAR treatment.

Example 4

Constitutively Active p38 Rescues DUSP4 Repression of PEPCK Transcription

Members of the DUSP family show differing specificities for the MAPK family of kinases. DUSP4 has been previously shown to dephosphorylate and inactivate the MAPK family members ERK and JNK, but not p38. Interestingly, both JNK and p38 have been shown to be positive regulators of gluconeogenesis, with p38 being downstream of PKA/cAMP, while DUSP4 shows the opposite effect (Cao et al. (2005) *J. Biol. Chem.* 280:42731-42737; Nakatani et al. (2004) *J. Biol. Chem.* 279:45803-45809). Since JNK and p38 have an inverse relationship to gluconeogenesis relative to DUSP4 it was tested whether the activity of either of these kinases is regulated by AICAR in H4IIE cells.

Figure 7:
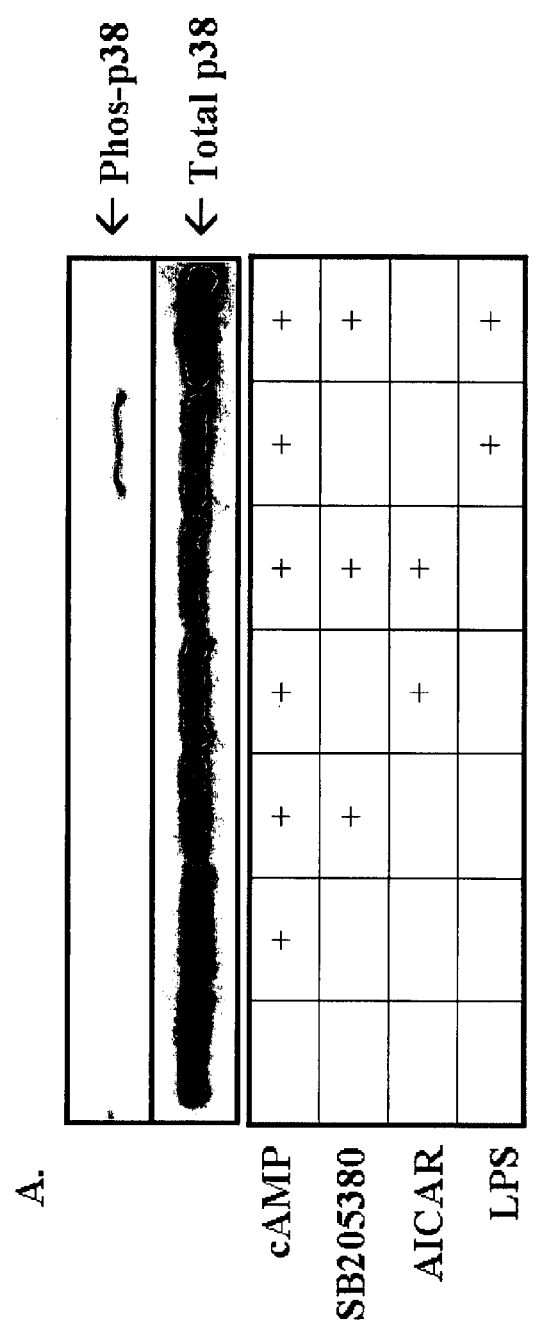
FIG. 7 demonstrates DUSP4 repression of PEPCK through p38. Panel A is a Western blot of H4IIE cells starved for 6 hours and then treated as indicated by the chart for 2 hours. SB205830 is a specific p38 chemical inhibitor. LPS is included as a positive control of p38 activation. Panel B is a schematic depiction of results from reporter assays performed as described for FIG. 5, above, except that the cells were treated as indicated by the chart in Panel B.
Figure 7:
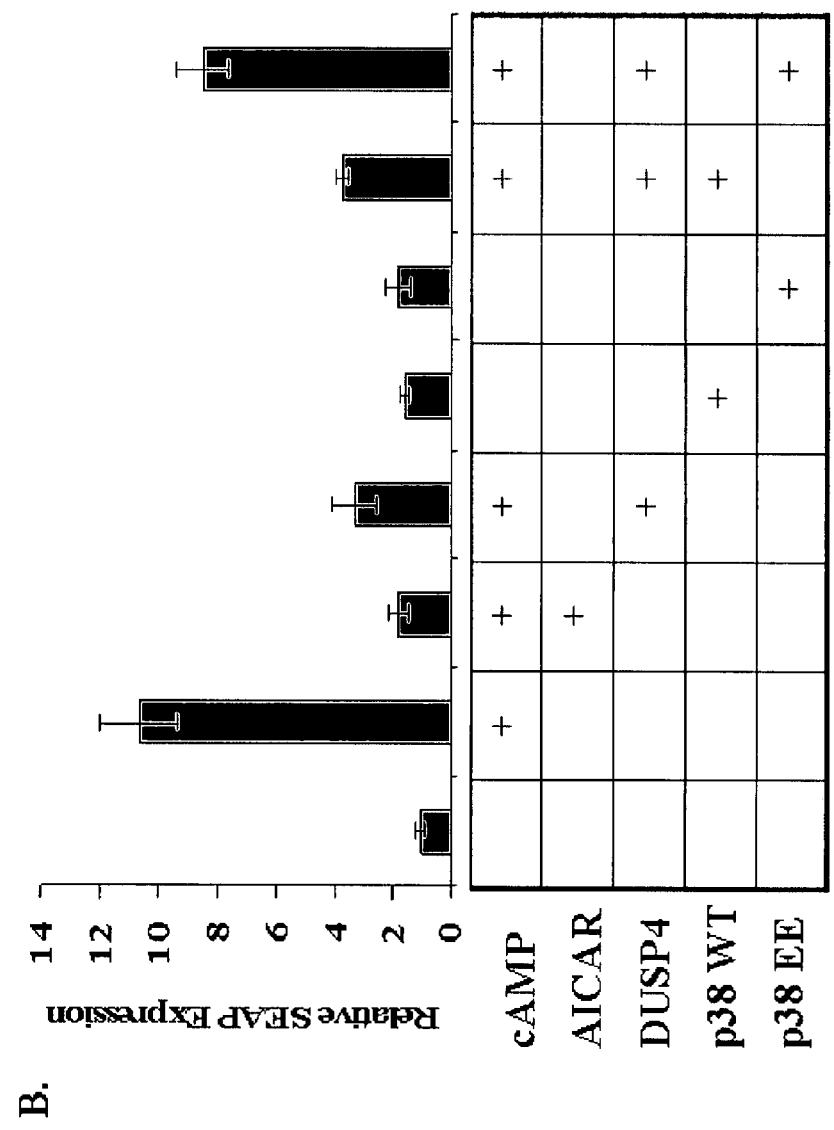

FIG. 7A includes a Western blot probed with anti-p38 or anti-phosphor-p38 antibodies (Cell Signaling Technology) at a 1:1000 dilution. The Western blot shows that addition of cAMP to serum starved H4IIE cells for 2 hours leads to an increase in the phosphorylation of p38 and that it is inhibited with the addition of either AICAR or a specific p38 chemical inhibitor SB205830. JNK activity was not inhibited by AICAR (data not shown).

Since the amount of active p38 present in the cAMP treated H4IIE cells decreases upon 2 hours of AICAR treatment, which corresponds to the time point of DUSP4 induction, a possible link between DUSP4 and p38 was examined. FIG. 7B shows that while AICAR and DUSP4 transfection repress cAMP activation of the PEPCK promoter, inclusion of constitutively active p38 (p38EE), but not WT p38, abrogates the ability of DUSP4 to repress the PEPCK promoter. p38EE, which is refractory to DUSP regulation, is unable to activate the PEPCK promoter on its own as well, indicating that active p38 is necessary but not sufficient for mediation of the cAMP effect on PEPCK. These data strongly suggest that DUSP4 is dephosphorylating and inactivating p38 upon its induction by AICAR, leading to a dampening of the cAMP signal to PEPCK.

Figure 8:
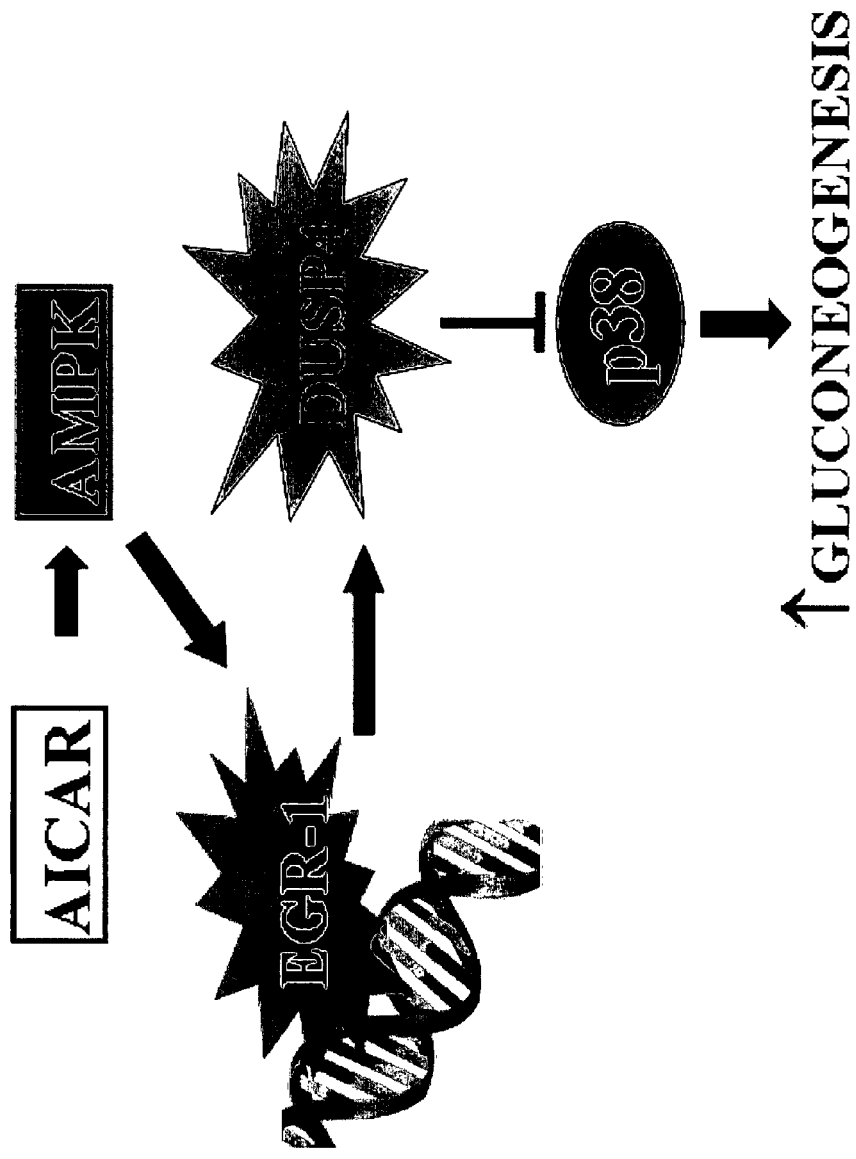
FIG. 8 is a schematic model of repression of glucose production via EGR1 and DUSP4. AMPK activation via AICAR results in transcriptional activation of DUSP4 by EGR1. DUSP4 is one target activated by EGR1 upon AMPK activation, but depletion of either results in a defect in the ability of AICAR to inhibit either PEPCK or G6P promoter activity and glucose production in hepatocyte cell lines. p38 can rescue DUSP4 inhibition of PEPCK.

These results lead to the model proposed in FIG. 8 where AICAR treatment of hepatocytes leads to activation and induction of EGR1 and DUSP4, which contribute to the inhibition of gluconeogenesis by repressing p38 activity. Neither the addition of exogenous DUSP4 nor the depletion of EGR1 can fully account for the effect of AICAR on hepatic glucose production, but the effect is significant.

The rescue of DUSP4 repression of PEPCK by a constitutively activated form of the MAPK p38, that is refractory to regulation by DUSPs, suggests that it is a target of DUSP4 action in this system. A recent study has shown that p38 is necessary for the cAMP dependent activation of gluconeogenic genes (Cao et al. (2005) *J. Biol. Chem.* 280:42731-42737). Blockade of p38 prevents transcription of PGC-1α and phosphorylation of CREB. Transcriptional up-regulation of DUSP4 following AICAR treatment could result in blockage of the necessary p38 mediated downstream events. Inhibition of cAMP-driven p38 phosphorylation by AICAR at 2 hours (the time of DUSP4 induction) of treatment also suggests this. This would be the first functional relationship between DUSP4 and p38 as previous studies have suggested that DUSP4 dephosphorylates solely ERK and JNK (Chu et al. (1996) *J. Biol. Chem.* 271:6497-6501; Chen et al. (2001) *J. Biol. Chem.* 276:29440-29449). Although JNK was also a potential target of DUSP4 due to its role in stimulating hepatic gluconeogenesis, JNK phosphorylation did not change upon cAMP or AICAR treatment in H4IIE cells. Two other members of the DUSP family have previously been implicated in gluconeogenesis. Surprisingly though, DUSP9 (MKP-4) and DUSP6 (MKP-3) activate PEPCK transcription (Xu et al. (2003) *J. Biol. Chem.* 278:30187-30192). DUSP9 inhibits insulin signaling and reverses insulin-induced repression of PEPCK while DUSP6 activates PEPCK in the presence of cAMP and dexamethasone and activates glucose production. Both are more highly expressed in insulin resistant tissues when compared to normal tissues. The ability of DUSP4 to repress PEPCK and G6P expression is opposite to that reported for other members of this family. Accordingly, gluconeogenesis treatments that target DUSP4 activity (e.g. by overexpression or inhibition) in a selective manner (i.e. preferentially targeting DUSP4 over DUSP6 and 9) may be preferred.

The foregoing description of the present invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

What is claimed is:

1. A method of reducing gluconeogenesis in a hepatocyte, the method comprising the step of administering to the hepatocyte a polypeptide having DUSP4 (Dual Specificity Phosphatase 4) activity, where in the polypeptide comprises an amino acid sequence having at least 90% global sequence identity to the amino acid sequence encoded by SEQ ID NO: 12.

2. The method of claim 1, wherein the DUSP4 polypeptide comprises the amino acid sequence encoded by SEQ ID NO: 12.

3. The method of claim 1, wherein the DUSP4 polypeptide is a fusion polypeptide comprising a DUSP4 polypeptide.

4. A method of reducing gluconeogenesis in a hepatocyte, the method comprising the step of administering to the hepatocyte a polypeptide comprising DUSP4 (Dual Specificity Phosphatase 4).

5. The method of claim 4, wherein the polypeptide comprising DUSP4 is selected from the group consisting of a DUSP4 polypeptide and a fusion polypeptide comprising a DUSP4 polypeptide.

6. A method of reducing gluconeogenesis in a subject in need thereof, comprising the step of administering to the subject a composition comprising a therapeutically effective amount of a polypeptide having at least 90% sequence identity to the polypeptide encoded by SEQ ID NO: 12 and dual specificity phosphatase 4 activity, wherein gluconeogenesis in the subject is reduced.

7. The method of claim 6, wherein the DUSP4 polypeptide comprises the amino acid sequence encoded by SEQ ID NO: 12.

8. The method of claim 6, wherein the DUSP4 polypeptide is a fusion polypeptide comprising a DUSP4 polypeptide.

* * * * *

SEQUENCE LISTING

<160> NUMBER OF SEQ ID NOS: 14

<210> SEQ ID NO 1
<211> LENGTH: 19
<212> TYPE: RNA
<213> ORGANISM: Artificial Sequence
<220> FEATURE:
<223> OTHER INFORMATION: Synthetic: DUSP4-targeting siRNA

<400> SEQUENCE: 1
gaucacggcu cuacugaau                                                    19

<210> SEQ ID NO 2
<211> LENGTH: 18
<212> TYPE: RNA
<213> ORGANISM: Artificial Sequence
<220> FEATURE:
<223> OTHER INFORMATION: Synthetic: DUSP4-targeting siRNA

<400> SEQUENCE: 2
caaaugaguc cuggauca                                                     18

<210> SEQ ID NO 3
<211> LENGTH: 19
<212> TYPE: RNA
<213> ORGANISM: Artificial Sequence
<220> FEATURE:
<223> OTHER INFORMATION: Synthetic: DUSP4-targeting siRNA

<400> SEQUENCE: 3
ggacauuacc aguacaagu                                                    19

<210> SEQ ID NO 4
<211> LENGTH: 19
<212> TYPE: RNA
<213> ORGANISM: Artificial Sequence
<220> FEATURE:
<223> OTHER INFORMATION: Synthetic: DUSP4-targeting siRNA

<400> SEQUENCE: 4
gugaacgugc gcugcaaua                                                    19

<210> SEQ ID NO 5
<211> LENGTH: 13
<212> TYPE: DNA
<213> ORGANISM: Homo sapiens

<400> SEQUENCE: 5
cgtgaccggg agc                                                          13

<210> SEQ ID NO 6
<211> LENGTH: 23
<212> TYPE: DNA
<213> ORGANISM: Artificial Sequence
<220> FEATURE:
<223> OTHER INFORMATION: Synthetic: PCR primer for rat DUSP4 promoter

<400> SEQUENCE: 6
ggcggctcca ttcacaaagt ccg                                               23

<210> SEQ ID NO 7
<211> LENGTH: 22
<212> TYPE: DNA
<213> ORGANISM: Artificial Sequence
<220> FEATURE:
<223> OTHER INFORMATION: Synthetic: PCR primer for rat DUSP4 promoter

<400> SEQUENCE: 7
ccgactcttg aatggagcgc cg                                          22

<210> SEQ ID NO 8
<211> LENGTH: 34
<212> TYPE: DNA
<213> ORGANISM: Artificial Sequence
<220> FEATURE:
<223> OTHER INFORMATION: Synthetic: PCR primer for rat PEPCK promoter

<400> SEQUENCE: 8
gcctcgagct cgagtccagc agacacctag tggg                             34

<210> SEQ ID NO 9
<211> LENGTH: 36
<212> TYPE: DNA
<213> ORGANISM: Artificial Sequence
<220> FEATURE:
<223> OTHER INFORMATION: Synthetic: PCR primer for rat PEPCK promoter

<400> SEQUENCE: 9
gcaagcttaa gctttctcgc cggatttccc ctgttc                           36

<210> SEQ ID NO 10
<211> LENGTH: 35
<212> TYPE: DNA
<213> ORGANISM: Artificial Sequence
<220> FEATURE:
<223> OTHER INFORMATION: Synthetic: PCR primer for human G6P promoter

<400> SEQUENCE: 10
gcctcgagct cgagtgagct caggaattca agacc                            35

<210> SEQ ID NO 11
<211> LENGTH: 35
<212> TYPE: DNA
<213> ORGANISM: Artificial Sequence
<220> FEATURE:
<223> OTHER INFORMATION: Synthetic: PCR primer for human G6P promoter

<400> SEQUENCE: 11
gcaagcttaa gcttagatgt cagcagagcc cttgc                            35

<210> SEQ ID NO 12
<211> LENGTH: 2498
<212> TYPE: DNA
<213> ORGANISM: Homo sapiens

<400> SEQUENCE: 12
gctgagcgcc ggaggagcgt aggcagggca gcgctggcgc cagtggcgac aggagccgcg    60
cgaccggcaa aaatacacgg gaggccgtcg ccgaaaagag tccgcggtcc tctctcgtaa   120
acacactctc ctccaccggc gcctccccct ccgctctgcg cgccgcccgg ctgggcgccc   180
gaggccgctc cgactgctat gtgaccgcga ggctgcggga ggaaggggac agggaagaag   240
aggctctccc gcgggagccc ttgaggacca agtttgcggc cacttctgca ggcgtccctt   300
cttagctctc gcccgcccct ttctgcagcc taggcggccc gggttctctt ctcttcctcg   360
cgcgcccagc cgcctcggtt cccggcgacc atggtgacga tggaggagct gcgggagatg   420
gactgcagtg tgctcaaaag gctgatgaac cgggacgaga atggcggcgg cgcgggcggc   480

-continued

```
agcggcagcc acggcaccct ggggctgccg agcggcggca agtgcctgct gctggactgc      540
agaccgttcc tggcgcacag cgcgggctac atcctaggtt cggtcaacgt gcgctgtaac      600
accatcgtgc ggcggcgggc taagggctcc gtgagcctgg agcagatcct gcccgccgag      660
gaggaggtac gcgcccgctt gcgctccggc ctctactcgg cggtcatcgt ctacgacgag      720
cgcagcccgc gcgccgagag cctccgcgag gacagcaccg tgtcgctggt ggtgcaggcg      780
ctgcgccgca acgccgagcg caccgacatc tgcctgctca aaggcggcta tgagaggttt      840
tcctccgagt acccagaatt ctgttctaaa accaaggccc tggcagccat cccacccccg      900 gttccccca gtgccacaga gcccttggac ctgggctgca gctcctgtgg accccacta       960 cacgaccagg ggggtcctgt ggagatcctt cccttcctct acctcggcag tgcctaccat     1020
gctgcccgga gagacatgct ggacgccctg gcatcacgg ctctgttgaa tgtctcctcg      1080
gactgcccaa accactttga aggacactat cagtacaagt gcatcccagt ggaagataac     1140
cacaaggccg acatcagctc ctggttcatg gaagccatag agtacatcga tgccgtgaag     1200
gactgccgtg ggcgcgtgct ggtgcactgc caggcgggca tctcgcggtc ggccaccatc     1260
tgcctggcct acctgatgat gaagaaacgg gtgaggctgg aggaggcctt cgagttcgtt     1320
aagcagcgcc gcagcatcat ctcgcccaac ttcagcttca tggggcagct gctgcagttc     1380
gagtcccagt gctggccac gtcctgtgct cggaggctg ctagccctc gggacccctg        1440 cgggagcggg gcaagacccc cgccacccc acctcgcagt tcgtcttcag ctttccggtc      1500
tccgtgggcg tgcactcggc ccccagcagc ctgccctacc tgcacagccc catcaccacc     1560
tctcccagct gttagagccg ccctgggggc cccagaacca gagctggctc ccagcaaggg     1620
taggacgggc cgcatgcggg cagaaagttg ggactgagca gctgggagca ggcgaccgag     1680
ctccttcccc atcatttctc cttggccaac gacgaggcca gccagaatgg caataaggac     1740
tccgaataca taataaaagc aaacagaaca ctccaactta gagcaataac ggctgccgca     1800
gcagccaggg aagaccttgg tttggtttat gtgtcagttt cacttttccg atagaaattt     1860
cttacctcat ttttttaagc agtaaggctt gaagtgatga aacccacaga tcctagcaaa     1920
tgtgcccaac cagctttact aaaggggag gaagggaggg caagggatg agaagacaag       1980 tttcccagaa gtgcctggtt ctgtgtactt gtcccttgt tgtcgttgtt gtagttaaag      2040
gaatttcatt ttttaaaga aatcttcgaa ggtgtggttt tcatttctca gtcaccaaca      2100
gatgaataat tatgcttaat aataaagtat ttattaagac tttcttcaga gtatgaaagt     2160
acaaaaagtc tagttacagt ggatttagaa tatatttatg ttgatgtcaa acagctgagc     2220
accgtagcat gcagatgtca aggcagttag gaagtaaatg gtgtcttgta gatatgtgca     2280
aggtagcatg atgagcaact tgagtttgtt gccactgaga agcaggcggg ttgggtggga     2340
ggaggaagaa agggaagaat taggtttgaa ttgcttttta aaaaaaaag aaaagaaaaa      2400 gacagcatct cactatgttg ccaaggctca tcttgagaag caggcgggtt gggtgggagg     2460
aggaagaaag ggaagaatta ggtttgaatt gctttttt                             2498
```

```
<210> SEQ ID NO 13
<211> LENGTH: 2050
<212> TYPE: DNA
<213> ORGANISM: Rattus norvegicus

<400> SEQUENCE: 13
aatagctcat tctttaactg aaaaaaccca taaacaaaat aagaaacgca gtgccatttt       60
ggaacccaag gtaacaagga aaattctcca cagatgattg cccctgcaa cgcccactgg      120
```

```
acccagaaaa gggtgttggg gacttcagag tgcagagagt ctgtaggaag ccttgaaaat      180
gggagttgga ggtgatctct ggagagccgc tctgcagaaa acaaagcaaa ggtaactgag      240
tggagagagg gtttaaccgg gggaaaggac cctgaggctt tggctgccct cgctgcctca      300
gtcaggcttc tactcgcaac ctgaaatgga atattcgacc tggccgctac caaaccccgt      360
aattcccttg ttcggtgatt aattcttgct aacaagactt ggcaagatct cggccgaata      420 attttggct tctgtaaggt ccccaccaca tgcgcgcata acctcctttc ttgccaaaat       480
caagcccttg ggaaattaaa tgtccccggg aaggtaaaag cggggtgcag atgctacgtg      540
acctggaaag agggatgtag aaactcgaat cgtctctgag cttattaaat ttgcctttta      600
aaaggtcact cttcgcatgg acacttttca acatcttcct tcgcaccaaa tgtagacctt      660
aacaattatt tccttagagg acattgcgtg tgagcaagag ggaggcgagg acttccacca      720
aagcggaaaa cctccgggta tatccctcct cccccccttc ccatggttaa ataatcaggt     780
tttaggaagc ttgggccgga gtgcttccca ttctcctgca cgggcacacc attcggccaa     840
ttaacgcccc cctctgggtt gtaaagtaac aaacccctac acctctcttt tgttattggg     900 cttttggcgcg aggacttccc tttcatcttt caaagtccgg ggtttgccca ggttccgcgg    960
gaagctataa aaccgatcta atagctccgg acggaaatcg atcacgcaaa tgtataaact    1020
aagtccgggg aatcgcatta aaacaaaac aagacacaac cggccggacc cgaagagcaa     1080
gctttagtcc ggcgagaaga ggtcccaagc cctgcggggt ggcagccata cagtgtcagg    1140
ttccacccag cgagacctcg gagacttggg gggcggggg ggagcgcagg ggtgaagacc     1200
tccacgctga gagcccaggc ctcggttagg cccgcgtcgc cacccgctac taacacaacg    1260
ccgaacgccg cgctccgggg ctgaggaagg acagggagcc gcacgcggc tccattcaca     1320 aagtccggga gcttccggct tgccggcggg tcggaggctg cctccttttt cctctaggtc    1380
tcggttttat gaatgggcct ggcagacagc accgagcgcc ctgtttactc ctctctttgt    1440
gacgtcgagt tcccgtgact gggtgcgagg gggccggcgc tccattcaag agtcggggtg    1500 ggggcgggc ggggagcttg cgtgggggc ggggcctgga gaggtagtaa tgactcttcc      1560
ctcccccggg agagccggcg agcattaata aatctctaag cagaggagga aactctggct    1620
ggggcagtgc gtgcagctcc ggcggagcgt tgggggaaaa cggcggtgcc taaggcagga    1680
gcagcctagc tagcaaaaca caccaggggc aacaaaccga gaggagccct ctctctcgta    1740
aacatactcc cctcctcggt cacttgctcc gggtgccgtg cgcccgcctg ctttggcgcc    1800
agagaaggct cggactgcta tgtaacgtcg aggctgcggg aggaggagga aggggtgttg    1860
ggagaagagc cttggggcca agtttgcggg tcacttcggc aggcgccttc ttagccttcg    1920
cctgttcctt cttgtagcct agctggcttg ggtgcccttg gtcttctccg gctccccagc    1980
tgctgtgctt tgccggcgac atggtgacga tggaggaact gcgggagatg gactgcagcg    2040
tgctcaaaag                                                           2050
```

<210> SEQ ID NO 14
<211> LENGTH: 2050
<212> TYPE: DNA
<213> ORGANISM: Homo sapiens

<400> SEQUENCE: 14

```
gcggctttga ccactgatct cccacccgga gtgcccgacg cccagggtcc tgccaccggg       60
cagcctcggt cagtccacag ttgtggctcc ttccagggcc tggactaggg tgagcacaag      120
```

-continued

```
ccttgagcgc aacatttaag aagggcgccg aaaagtcagt aatcaaaaga aatatcttga        180
tgcaatgcct cttaaaaga aaaaaaaatg caaaaaatcc atgatgaata aaatactaaa        240
ttttaaaaag agaaaggatc cgtgcagtgc catcgtaagc catttttggag cccggagcaa       300 aaggaaatat caccttgccc aagcggtgcc cctacagctc atccgagtag ggcccggggg       360
tcgaggcatt cggggcccag tgggggacga ggccagtcga aggtctcgga agtggaggct       420
ccgccgagct ccggtcgggg agtgcaggga tggccccgg accggaggt gagagctcgg         480 gaaagccgct ccgcccggaa caaaggcatg gggagagggt gagcttgggc gggagagacc       540
cggcgggtac cggtgccctc gctgcctggg tcgggcttcc acgcgcgccc cggaatggaa       600
tacgctactc tgcagcctcc gaaactgcga gcgagtcctg taactccctt gctctgtgat       660
taattctcac taacaagact tggcaagatg tcggcgaat gattttttggc ttctgcacgg       720 tccccaccgc gtgcgtgcac aaaccccag ccaaaagccg cctctgggaa attaaatgca        780
aaagagaaat ggggatgggg agggctgcta cgtgaccagg aaaaagggat gcccagaaac      840
atgaatcgga cccagagctg ctgaagtcct ttcaaaaggt cattcttttgc gggtacatt      900 tccagggtcc agctccgcaa caaatgtgga ccctgtcatt tcctgaaagg ataattcaca      960
actatgcaag atagggtgaa gacgtttccc aaacccgaaa accttgtttt tcccccgacc      1020
agggttaaat aaacatcttt taggaagcgt ggacaggagc gcagcctgct ctcctccctc      1080
ggaacaccat tccggcaatt aatgcctccc tttgggtagt aaagcaacaa accccacacc     1140
tcactccgat cctgggcttc gggcgggagg actttctctt tcatcttcca agcagggggt      1200
tgcccacgtt cttggggaag ctataaaact gatttaatgg ctttagatga aaatcgatca      1260
cgctaatgca tacgctaacg tctcaggaat cgcatattca gaaggactg gccgggccga       1320 aagcgcacgg ggagtctggg gctaggaggt gtcaggcccc gctgggtggg cagcagcgct     1380
ccggtcccct ctccacttgg gtaaccggga aaaacctacg gggctgtcac gcggggaagc     1440
gcgaaggtgc caagggatga aagctcaaac ccgagccctg gcctcctcag ccggctattt     1500
cctttggcgc cgcccgccta gcggcggggt gcagcggcgg cacaggtgcc ggtgtcgggc     1560
tggaggcgcg gcgcaggctg ggcccgcggg tagacggcga aaggcgccgc gcgctccatt    1620
cacaaagtcc gggcgctgcc cgccgctggc ggcgggtcgg aggccgcctc cctcttcctc      1680
tcggcctcgg ttttatgaat gggcctgatg gcgagcaccc ggcgccctgt ttactccgct     1740
ctttgtgacg tcgagttccc gtgacccgga gccagcggcc gcgctccatt caagctccgg    1800
ggagggggtg ggaggagggg cccggagggg gcggggagtc agcgcggggg gcggggggaca   1860 gcgcgggggg cggggggacgg cgcggggccc ggaatggaac ggggcggggc ctggcgggggt  1920 agtacctagc gcccccctccc ccgggagcgc ggaggagcat taataaacct ctaagccgag    1980
gagaaaactc tggctggggc agtgcgctga gcgccggagg agcgtaggca gggcagcgct   2040
ggcgccagtg                                                             2050
```